United States Patent [19]

Meyer

[11] Patent Number: 5,648,482

[45] Date of Patent: Jul. 15, 1997

[54] PRIMERS TARGETED TO CYP2D6 GENE FOR DETECTING POOR METABOLIZERS OF DRUGS

[75] Inventor: Urs Albert Meyer, Oberwil, Switzerland

[73] Assignee: Hoffmann-La Roche Inc., Nutley, N.J.

[21] Appl. No.: 204,697

[22] Filed: Mar. 2, 1994

Related U.S. Application Data

[63] Continuation of Ser. No. 716,500, Jun. 17, 1991, abandoned.

[30] Foreign Application Priority Data

| Jun. 22, 1990 | [EP] | European Pat. Off. ............... 90810467 |
| May 29, 1991 | [EP] | European Pat. Off. ............... 91108867 |

[51] Int. Cl.$^6$ ........................... C07H 21/04; C12P 19/34; C12Q 1/68
[52] U.S. Cl. ................. 536/24.33; 435/6; 435/91.1; 435/91.2; 536/23.1; 536/23.5; 536/24.3; 536/24.31; 935/76; 935/77; 935/78
[58] Field of Search ................. 435/6, 91.1, 91.2; 536/23.1, 23.5, 24.3, 24.31, 24.33; 935/76, 77, 78

[56] References Cited

U.S. PATENT DOCUMENTS

| 4,683,195 | 7/1987 | Mullis et al. ............... 435/91 |
| 4,683,202 | 7/1987 | Mullis ............... 435/91 |
| 5,508,199 | 4/1996 | Gonzalez ............... 435/320.1 |

FOREIGN PATENT DOCUMENTS

| 258 017 | 3/1988 | European Pat. Off. . |
| 297 379 | 1/1989 | European Pat. Off. . |
| 0332435 | 9/1989 | European Pat. Off. . |

OTHER PUBLICATIONS

Heim et al., Lancet 336:529–532 (1990).
Heim et al., Lancet 337:363 (1991).
Blum et al., Proc. Natl. Acad. Sci. USA 88:5237–5241 (1991).
Meyer et al., Pharmac. Ther. 46:297–308 (1990).
Gonzalez et al., Genomics 2:174–179 (1988).
Kimura et al., Am. J. Hum. Gen. 45:889–904 (1989).
Skoda al., Proc. Natl. Acad. Sci. USA 85:5240–5243 (1988).
Saiki et al., Science 230:1350–1354 (1985).
Saiki et al., Science 239:487–491 (1988).
Gaedigk et al., Naunyn–Schmiedeberg's Archives of Pharm. 341 (Supplement), Abstract 435 (1990).
Blum et al., DNA and Cell Biology 9:193–203 (1990).
Ohsako et al., J. Biol. Chem. 265:4530–4634 (1990).
Gonzalez et al., Chem. Abs. 112:266 abstract No. 71647h (1990).
Gonzalez et al., (1989) Derwent Publication, PB89–189013.
Katagiri, Patent Abstracts of Japan 12:56 (C–477) (1988).
Manns et al., J. Clin. Invest. 83:1066–1072 (1989).
Gonzalez et al., Nature 331:442–446 (1988).
Traber et al., Mol. Pharm. 37:810–819 (1990).
Ruano et al., NAR 17:8392 (1989).
Okayama et al., J. Lab. Clin. Med. 114:105–113 (1989).
Wu et al., Proc. Natl. Acad. Sci. USA 86:2757–2760 (1989).
Newton et al., NAR 17:2502–2516 (1989).
Sarkar et al., Anal. Biochem. 186:64–68 (1990).
Gyllenstein et al., Proc. Natl. Acad. Sci. USA 85:7652–7656 (1989).
Linz et al., J. Clin. Chem. Clin. Biochem. 28:5–13 (1990).
Kwok et al., NAR 18:999–1005 (1990).
Blum et al., NAR 17:3589 (1989).

*Primary Examiner*—Stephanie W. Zitomer
*Assistant Examiner*—Paul B. Tran
*Attorney, Agent, or Firm*—George W. Johnston; Dennis P. Tramaloni; Bruce A. Pokras

[57] ABSTRACT

A method for the detection of poor metabolizers of drugs using PCR technology is described comprising a) optionally amplifying a gene coding for an enzyme known to be responsible for the metabolization of drugs, thereby separating it from possible closely related pseudogens, b) amplifying different allelic forms of the gene of step a) and c) detecting the product of step b). Primers for amplification of the genes responsible for the debrisoquine or acetylation phenotype are also disclosed.

5 Claims, 12 Drawing Sheets

STRUCTURE OF THE P450 II D6-8 GENE CLUSTER

STRUCTURE OF MOST ABUNDANT P450 II D6 ALLELES a) ACTIVE a) DEFECTIVE

TYPE OF MUTATIONS
NUCLEOTIDE DELETON
IN EXON 5 (2637A)

SPLICE SITE DEFECT
(1934 G-A), AA CHANGES

DELETION OF D6

SAME MUTATIONS
AS 29B IN D6

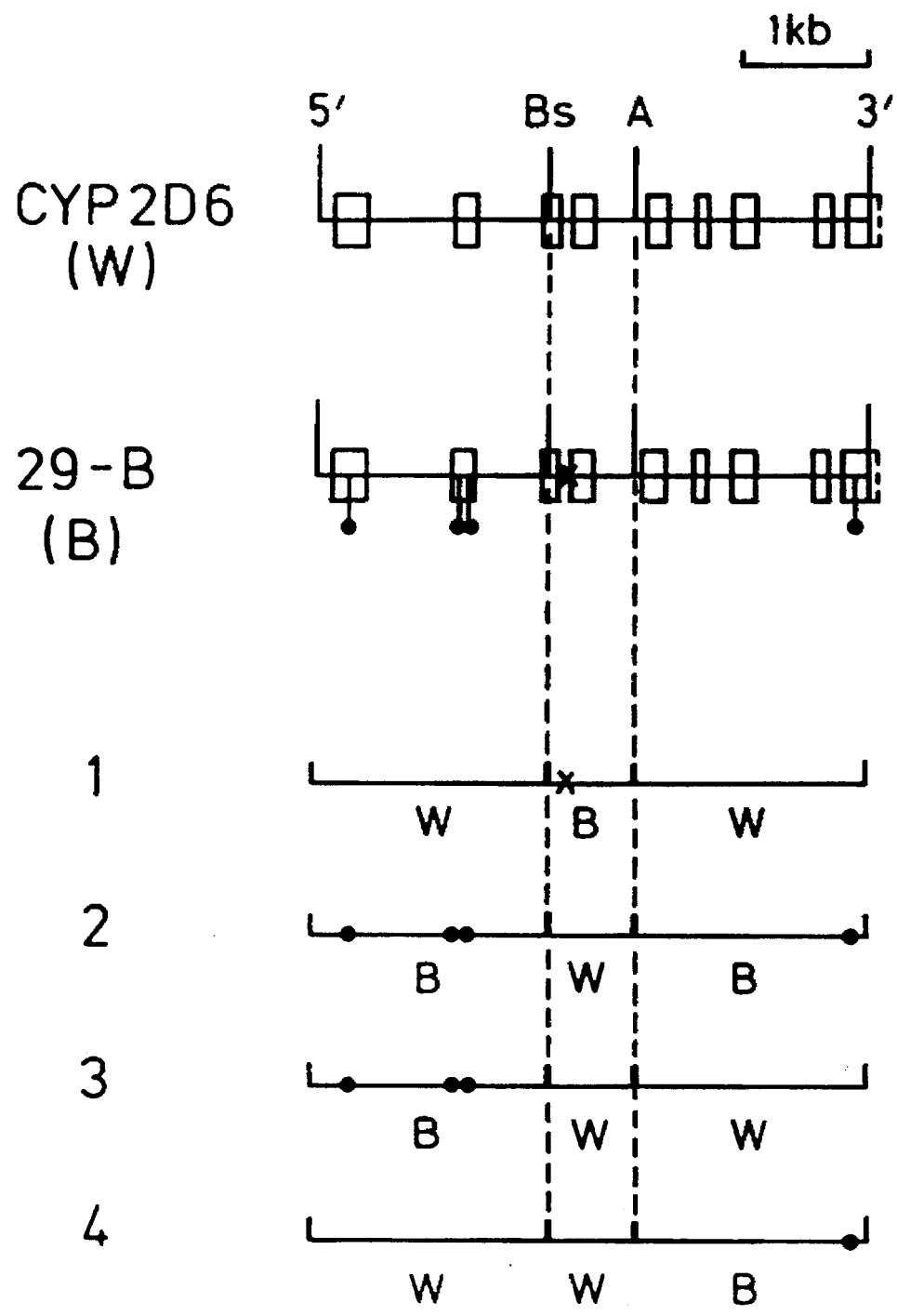
F I G. 6A cDNA

EXPRESSION

CYP2D6 SPECIFIC AMPLFICATION OF DNA-FRAGMENTS

PRINCIPLE OF ALLELE SPECIFIC AMPLIFICATION

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

ATTTCCAGC TGGAATCC                                                          18

( 2 ) INFORMATION FOR SEQ ID NO:2:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

GAGACTCCTC GGTCTCTC                                                         18

( 2 ) INFORMATION FOR SEQ ID NO:3:

( i ) SEQUENCE CHARACTERISTICS:
       ( A ) LENGTH: 14 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

CGAAAGGGGC GTCC                                                             14

( 2 ) INFORMATION FOR SEQ ID NO:4:

( i ) SEQUENCE CHARACTERISTICS:
   ( A ) LENGTH: 14 base pairs
   ( B ) TYPE: nucleic acid
   ( C ) STRANDEDNESS: single
   ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

CGAAAGGGGC GTCT 14

( 2 ) INFORMATION FOR SEQ ID NO:5:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

GCGGAGCGAG AGACCGAGGA 20

( 2 ) INFORMATION FOR SEQ ID NO:6:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

CCGGCCCTGA CACTCCTTCT 20

( 2 ) INFORMATION FOR SEQ ID NO:7:

( i ) SEQUENCE CHARACTERISTICS:
      ( A ) LENGTH: 14 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

GCTAACTGAG CACA 14

( 2 ) INFORMATION FOR SEQ ID NO:8:

( i ) SEQUENCE CHARACTERISTICS:
      ( A ) LENGTH: 14 base pairs
      ( B ) TYPE: nucleic acid
      ( C ) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

GCTAACTGAG CACG               14

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

AATTAGTCAC ACGAGGA               17

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

CTGATTTGGT CCAG               14

(2) INFORMATION FOR SEQ ID NO:11:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

CTGATTTGGT CCAA               14

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA ( i i i ) HYPOTHETICAL: NO ( i v ) ANTI-SENSE: NO ( x i ) SEQUENCE DESCRIPTION: SEQ ID NO:12:

TCTAGCATGA ATCACTCTGC 20

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

TTTACGCTTG AACCTCG 17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

TTTACGCTTG AACCTCA 17

( 2 ) INFORMATION FOR SEQ ID NO:15:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

AATAGTAAGG GATC 14

( 2 ) INFORMATION FOR SEQ ID NO:16:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

AATAGTAAGG GATT  14

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

GGGTCACCAT CGCCTCGCG  19

( 2 ) INFORMATION FOR SEQ ID NO:18:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

TCCTCGCCGC GGGTCACCA  19

PRIMERS TARGETED TO CYP2D6 GENE FOR DETECTING POOR METABOLIZERS OF DRUGS

This is a continuation of application Ser. No. 07/716,500 filed Jun. 17, 1991, now abandoned.

BACKGROUND OF THE INVENTION

The present invention relates to primers for the detection of genes for drug metabolizing enzymes, especially for the detection of the presence or absence of mutated nucleotide sequences within the genes of "poor metabolizers" (PMs) of drugs. The invention further relates to a method and a diagnostic kit for the detection of such genes or nucleotide sequences using Polymerase Chain Reaction (PCR)-technology.

Polymorphic genes play an important role as causes of interindividual variation in drug metabolism and in the occurrence of side effects and therapeutic failures. Moreover, they serve as genetic markers for numerous diseases. The elucidation of these mutations therefore has clinical importance and routine phenotyping has been recommended particularly for psychiatric patients and for volunteers in clinical studies (Gram and Brøsen, European Consensus Conference on Pharmacogenetics, Commission of the European Communities, Luxembourg, 1990, pp. 87–96; Balant et al., Eur. J. Clin. Pharmacol. 36, 551–554 [1989]). Moreover, recent studies have indicated that a link may exist between the debrisoquine phenotype and some forms of cancer (Caporaso et al., Cancer Research 49, 3675–3679 [1989]).

The existence of the polymorphic oxidation of debrisoquine and sparteine reported by Mahgoub et al., Lancet 1977, pages 584–586 and Eichelbaum et al., Eur. J. Clin. Pharmacol. 16, 183–187 [1979], caused a resurgence of interest in genetic factors influencing the individual response to drugs. Today, the debrisoquine polymorphism probably is one of the best studied variations of drug metabolism. In this case, the so-called "poor metabolizer" (hereinafter referred to as PM) phenotype is inherited as an autosomal-recessive trait and occurs with a frequency of 5–10% in the European and North American population (Meyer et al., Advances in Drug Research 19, 197–241 [1989] and Eichelbaum, ISI Atlas of Science; 243–251 [1988]). Phenotype means a physical or behavioral trait of an organism. In the case of debrisoquine polymorphism, the PM-phenotype is associated with the inability of efficient metabolization of over 25 drugs, including antiarrhythmics (e.g. flecainide and propafenone), antidepressants (e.g. imipramine, nortriptyline, clomipramine), neuroleptics (e.g. perphenazine and thioridazine), antianginals (perhexiline) and opioids (e.g. dextromethorphan and codeine (Meyer et al., Pharmac. Ther. 46, 297–308 [1990]). People who suffer from this deficiency of drug metabolism often experience exaggerated pharmacological or toxic responses when they are treated with usual doses of drugs.

In addition to the debrisoquine polymorphism, two other genetic polymorphisms of drug metabolism have been studied at the molecular level. These are the mephenytoin polymorphism which is located within the P450IIC subfamily and the acetylation polymorphism (Meyer et al., Advances in Drug Research 19, 197–241 [1989]). The reasons for these metabolic disorders seem to be the same as for the debrisoquine polymorphism in that distinct mutations in corresponding genes coding for the metabolizing enzymes do exist.

Previous studies have revealed that the debrisoquine PM phenotype is caused by the absence in the liver of a specific cytochrome P450 isozyme, designated P450IID6 (Nebert et al., DNA 8, 1–13 [1989]) or P450dbl (Zanger et al., Biochemistry 27, 5447–5454 [1988]). The gene for P450IID6, designated CYP2D6 (Nebert et al., supra), has been localized to chromosome 22 (Gonzalez et al., Genomics 2, 174–179 [1988]). A presumed pseudogene CYP2D7 and a definite pseudogene CYP2D8 are localized 5' of the CYP2D6 locus (FIG. 1), (Kimura et al., Am. J. Hum. Gem 45, 889–904 [1989]). Aberrant splicing of its premRNA was observed in livers of PMs and could explain its absence (Gonzalez et al., Nature 331,442–446 [1988]). These publications by Gonzalez et al. or Kimura et al. mentioned above describe cDNA's (and not genomic DNA sequences) which do not define specific mutations of the CYP2D6 gene which would allow the determination of the genotype and the assignment of the corresponding debrisoquine phenotype. In further studies, using restriction fragment length polymorphism (RFLP) analysis of leukocyte DNA, several mutant alleles of the P450IID6 gene locus (CYP2D) associated with the PM-phenotype were identified (Skoda et al., Proc. Natl. Acad. Sci. USA 85, 5240–5243 [1988]). After digestion of genomic DNA with the restriction enzyme XbaI these two alleles produced characteristic fragments of 11.5 kb and 44 kb respectively (FIG. 2). However, only the genotypes 44/44 kb, 44/11.5 kb or 11.5/11.5 kb so far predicted the PM-phenotype. It had been hoped that RFLP analysis would allow genotyping of all the PMs. In practice only 25% of PMs could be predicted after tests with numerous restriction endonucleases. All the extensive metabolizers (EM) and the remainder of PMs (75%) had one or two 29 kb fragments which can represent both an active (wild-type) or defective allele. Therefore, the RFLP-patterns have the disadvantage of being noninformative in regard to phenotype. To account for all mutant alleles, those represented by XbaI-29kb fragments therefore need further genomic characterization.

Previously the phenotype was determined by the administration of a test drug (debrisoquine, sparteine or dextrometorphan) followed by collection of urine for several hours and determination of the ratio between parent drug and its metabolite (urinary metabolic ratio). This procedure has considerable limitations because of adverse drug reactions, drug interactions and the confounding effect of diseases. Identification of the mutant genes causing the PM phenotype (i.e. the genotype) followed by the development of tests for the detection of the respective genotype, is therefore desired.

The acetylation polymorphism is also a classical example of a genetic defect in drug metabolism. It was observed over a quarter of a century ago with the advent of isoniazid therapy for tuberculosis by Hughes et al. (Am. Rev. Respir. Dis., 70, 266–273 [19541]). Patients could be classified as "rapid" ("fast") or "slow" eliminators of isoniazid and family studies revealed that the ability to eliminate isoniazid was determined by two alleles at a single autosomal gene locus, slow acetylators being homozygous for a recessive allele as described by Evans et al. in Br. Med. Jr., 2, 485–491 (1960). The polymorphism of N-acetylation has recently been reviewed by Meyer et al. in Advances in Drug Research 19, 197–241 (1989).

The proportions of rapid (RA) and slow acetylators (SA) vary remarkably in different ethnic and/or geographic populations. For example, the percentage of slow acetylators among Canadian Eskimos is 5%, whereas it rises to 83% among Egyptians and 90% among Moroccans. Most populations in Europe and North America have an approximately equal number of rapid and slow acetylators.

Numerous subsequent studies have demonstrated that the acetylation polymorphism affects the metabolism of a wide variety of other arylamine and hydrazine drugs and numerous foreign chemicals. These include the drugs sulfamethazine (SMZ) and several other sulfonamides, hydralazine, procainamide, dapsone, p-aminobenzoic acid (PABA), phenelzine and aminoglutethimide. The polymorphism also involves the metabolism of caffeine, clonazepam and nitrazepam as well as the potential arylamine carcinogens benzidine, 2-aminoflorene and β-naphthylamine.

The phenotyping procedures in case of the acetylation polymorphism using isonazid were later replaced by testing with sulfamethazine or dapsone. More recently, a phenotyping procedure using caffeine as a test substance has been developed and described by Grant et al. in Brit. J. Clin. Pharmacol. 17, 459–464 (1984) and further refined by Tang et al. as described in Clin. Pharmacol. Ther. 42, 509–513 (1987). These procedures have the same practical limitations as described above for the debrisoquine polymorphism. A more practical and unambiguous procedure for the determination of this polymorphism is therefore desired.

Recently the gene coding for the human hepatic arylamine N-acetyltransferase (NAT), which is responsible for the acetylation polymorphism described above, has been cloned from human leukocyte DNA by Blum et al. (DNA and Cell Biology 9, 193–203 The sequences of these genes have the following designations and accession numbers in the EMBL data library: NAT1, hgnat-a, X17059; NAT2, hgnat-b, X14672. Two genes, designated NAT1 and NAT2, have been assigned to human chromosome 8, pter-q11. The product of the NAT2 gene had an identical apparent molecular weight as the NAT protein detected in human liver cytosol. The two human genes, NAT1 and NAT2, encoding two NAT proteins were cloned and characterized. The numbers given to the base sequences of NAT1 and NAT2 were also used in this specification. NAT2 was identified as the gene encoding the polymorphic NAT2 isozyme. Knowing the mutations of the allelic variants of the NAT2 gene would allow the development of methods for the detection of the genotype instead of the PM phenotype.

DESCRIPTION OF THE FIGURES

FIG. 1A: The cluster contains the functional CYP2D6 gene and the probably nonfunctional CYP2D7 and the definitely nonfunctional CYP2D8 genes. Exons are numbered 1–9. Restriction sites for different endonucleases are marked as E, EcoRI; B, BamHI; H; HindIII; X; XbaI.

FIG. 1B: The active 29-wt (wild-type) allele and the four most abundant defective alleles are schematically shown. The 29-A and the 29-B alleles have point mutations in the CYP2D6 gene. The 11.5 kb allele has lost the entire CYP2D6 gene. The 44 kb allele has an additional yet unknown gene and mutant CYP2D6 gene, at least in Caucasians.

At least four alleles can be identified by RFLP-analysis of human genomic DNA after digestion with the restriction endonuclease XbaI. A radiolabeled P450IID6-cDNA was used as probe. Three alleles were identified as fragments of 44 kb, 29 kb and 11.5 kb. One allele was designated 16+9, since these two fragments were always seen in combination. These alleles occur in a homozygous or heterozygous arrangement.

Figure 1A:
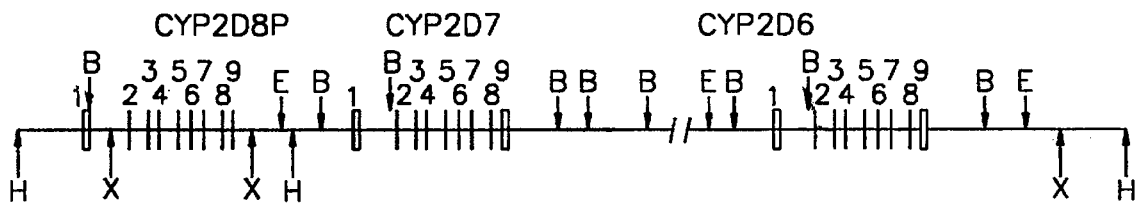
FIG. 1A and 1B show the structure of the CYP2D6-8 gene cluster and its most abundant alleles.
Figure 1B:
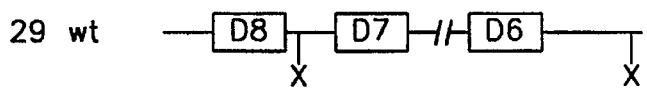
Figure 1B:
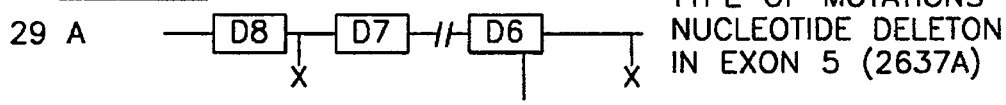
Figure 1B:
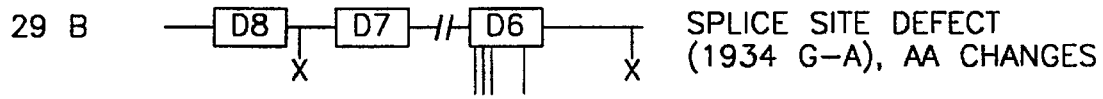
Figure 1B:
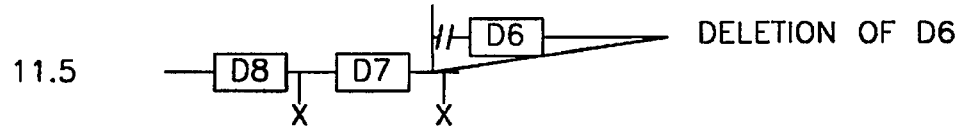
Figure 1B:
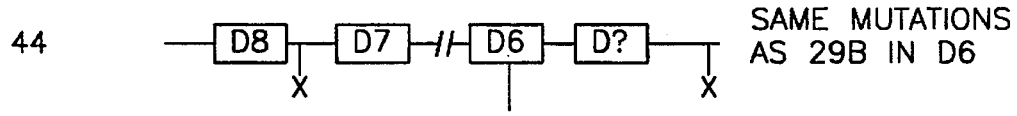
Figure 1B:
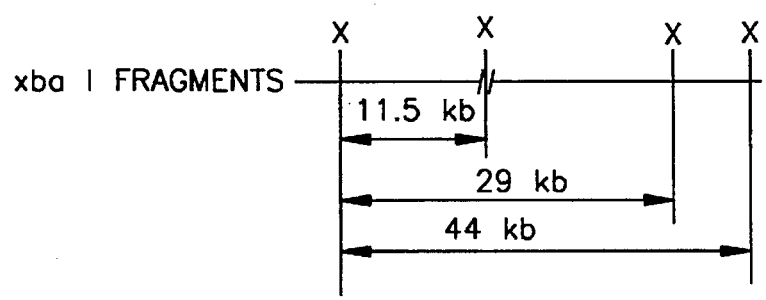
Figure 2:
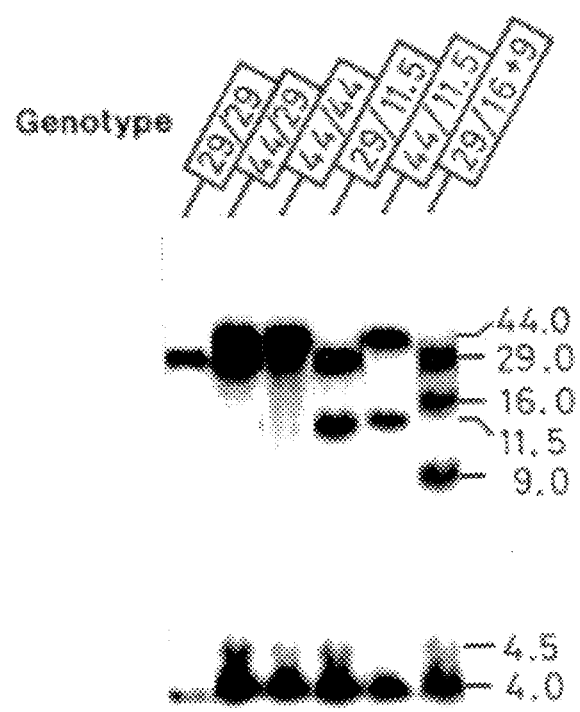
FIG. 2 illustrates RFLP-Analysis of Human DNA.
Figure 3:
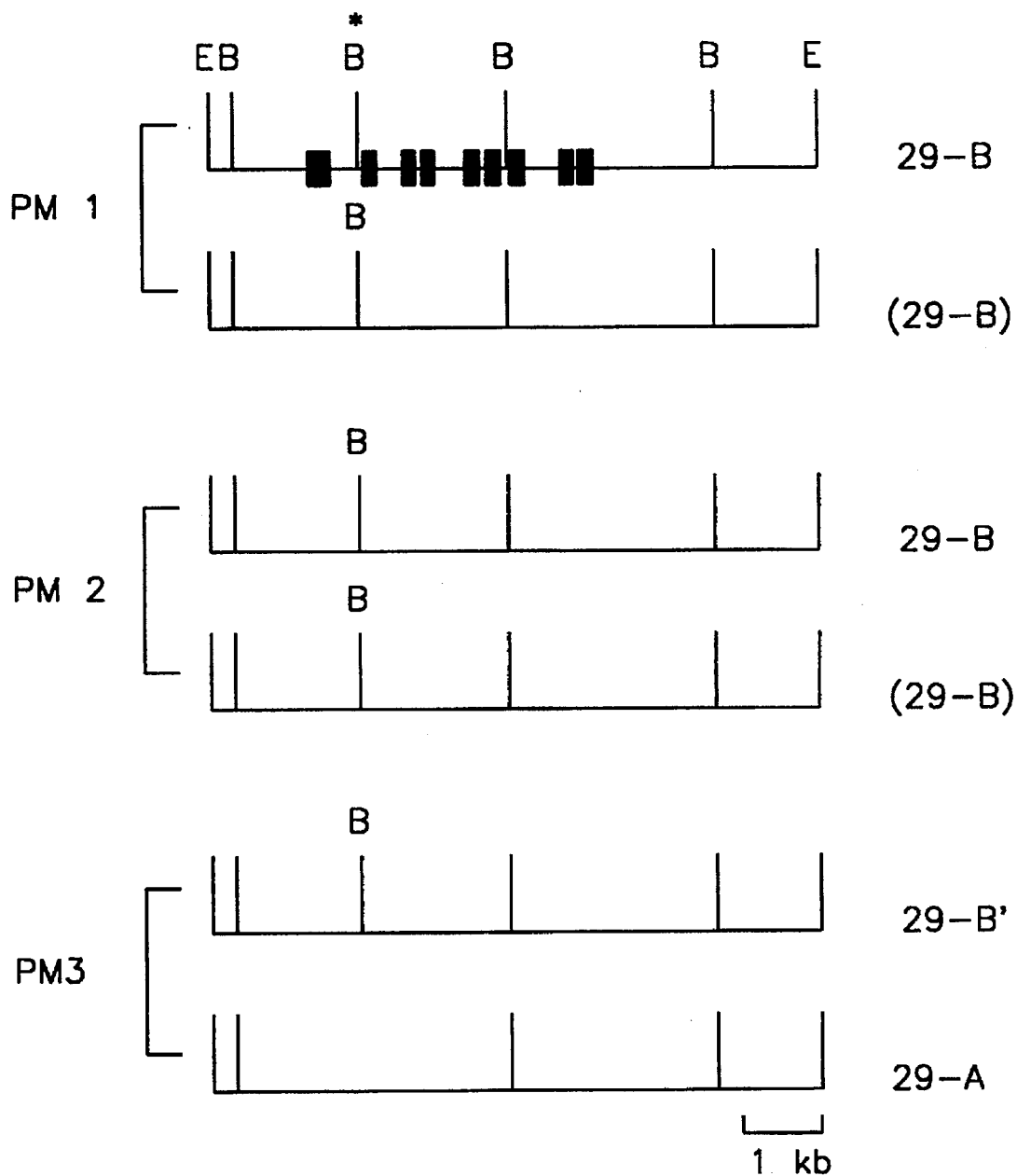

FIG. 3 illustrates restriction analysis of genomic DNA clones of three poor metabolizers of debrisoquine.

Two clones from each individual containing the 9.4 kb EcoRI fragment with the CYP2D6 gene were analysed. E, EcoRI; B, BamHI. The star indicates the additional BamHI site found in the alleles designated 29-B and 29-B': All the exons and intron-exon junctions were sequenced, except for the two clones 29-B, which are indicated in parentheses, where only the areas with mutations were sequenced.

Figure 4A:
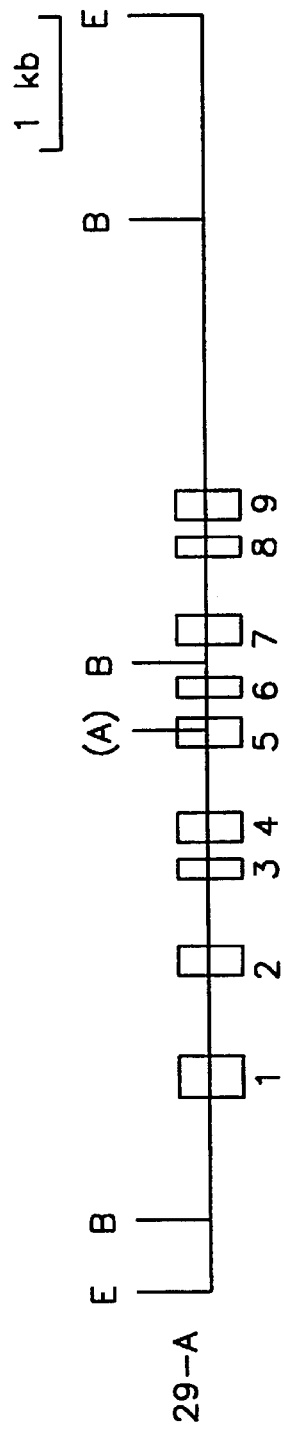
Figure 4B:
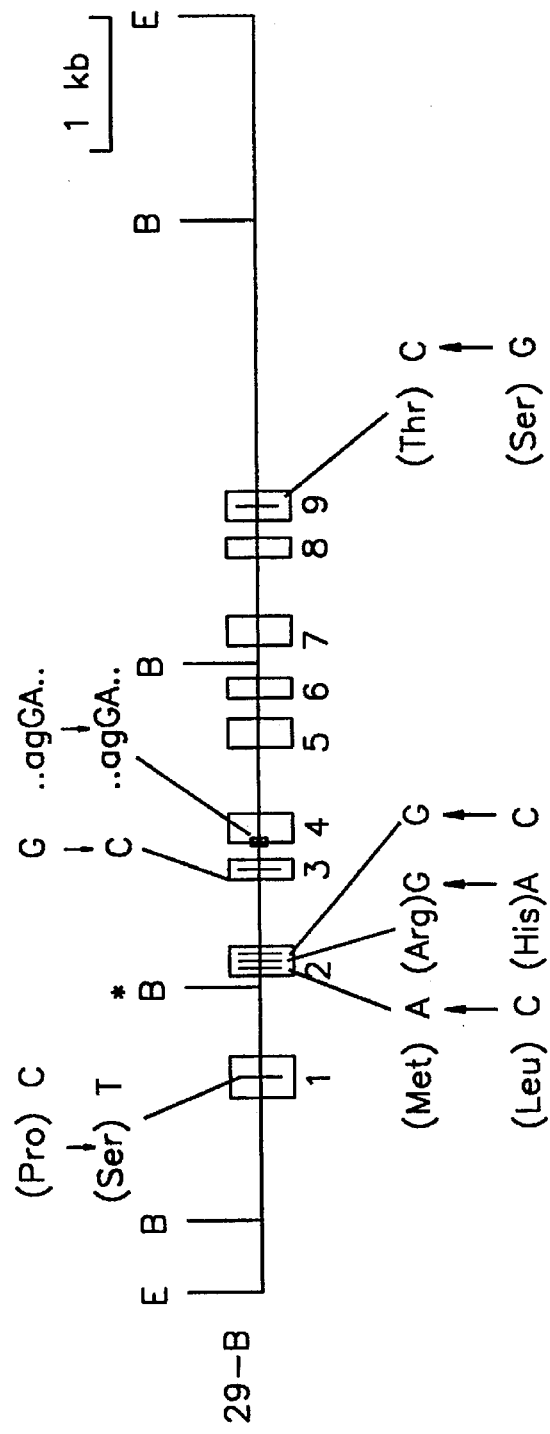

FIG. 4 shows the localization of mutations of two alleles (29-A, 29-B) of the CYP2D6 gene.

The star indicates the additional BamHI site (B). The exact locations of all mutations are given below in Example 1B.

Figure 5:
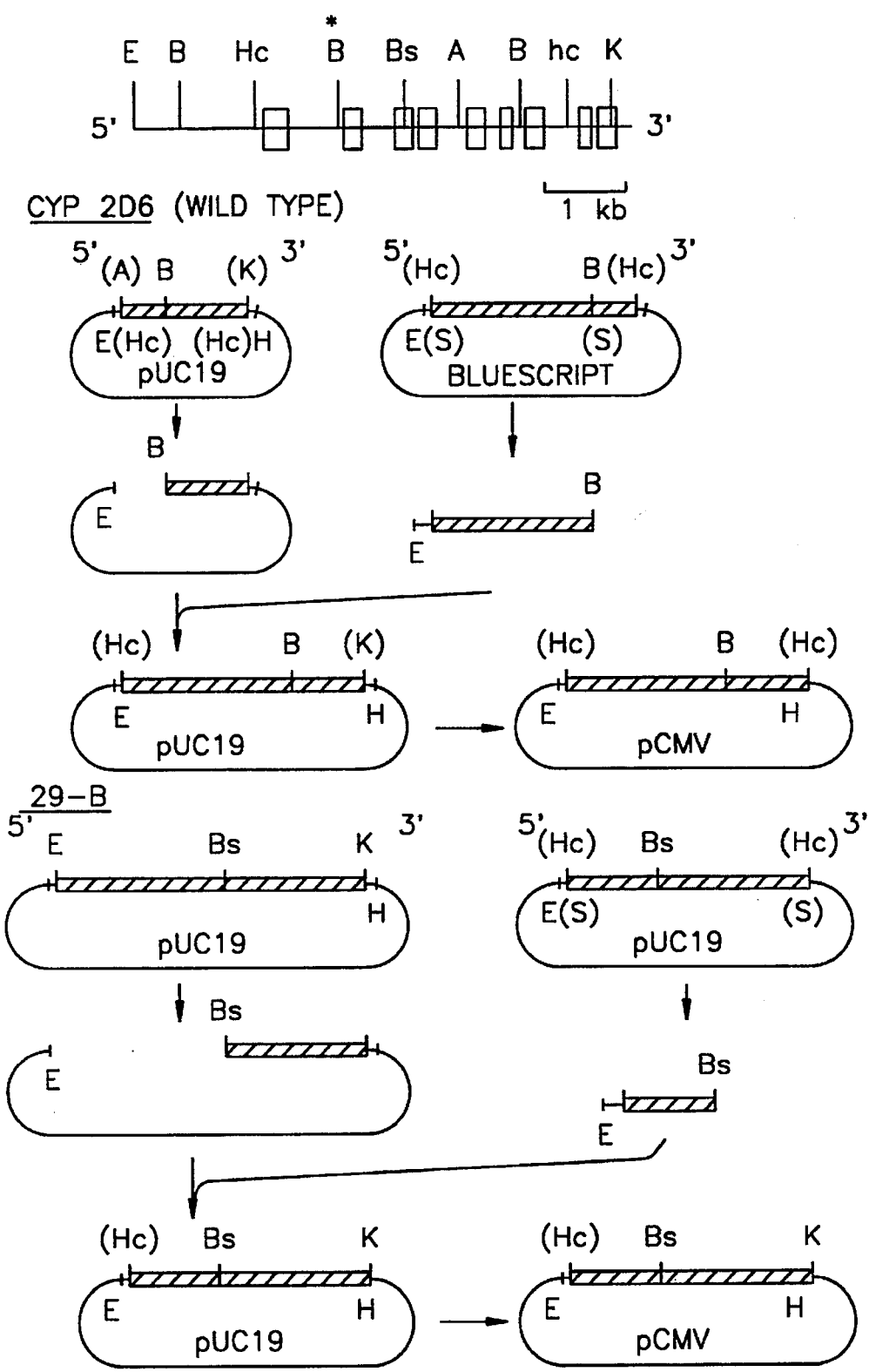

FIG. 5 is a schematic description of the construction of the eukaryotic expression vector pCMV containing the wild-type and chimeric CYP2D6 genes.

The procedure and the vector are detailed in Example 1. E, EcoRI; B, BamHI; Hc, HincII; Bs, BssHII; A, AccI; K, KpnI; S, SmaI; H, HindIII. The chimeric genes of FIG. 6 were assembled in pUC19 using combinations of the three parts E-Bs (1.8 kb), Bs-A (0.8 kb) and A-H (1.8 kb).

FIG. 6 illustrates the expression of chimeric gene-constructs from wild-type CYP2D6 and its mutant 29-B allele in COS-1 Cells.

FIG. 6A, is a description of the three parts of the wild-type (W) gene which were exchanged with the corresponding parts of the 29-B allele (B) with mutations. The mutations causing amino acid changes in exon 1, 2 and 9 are indicated by o, the mutation in the splice-site consensus sequence of the 3d intron by x.

Figure 6B:
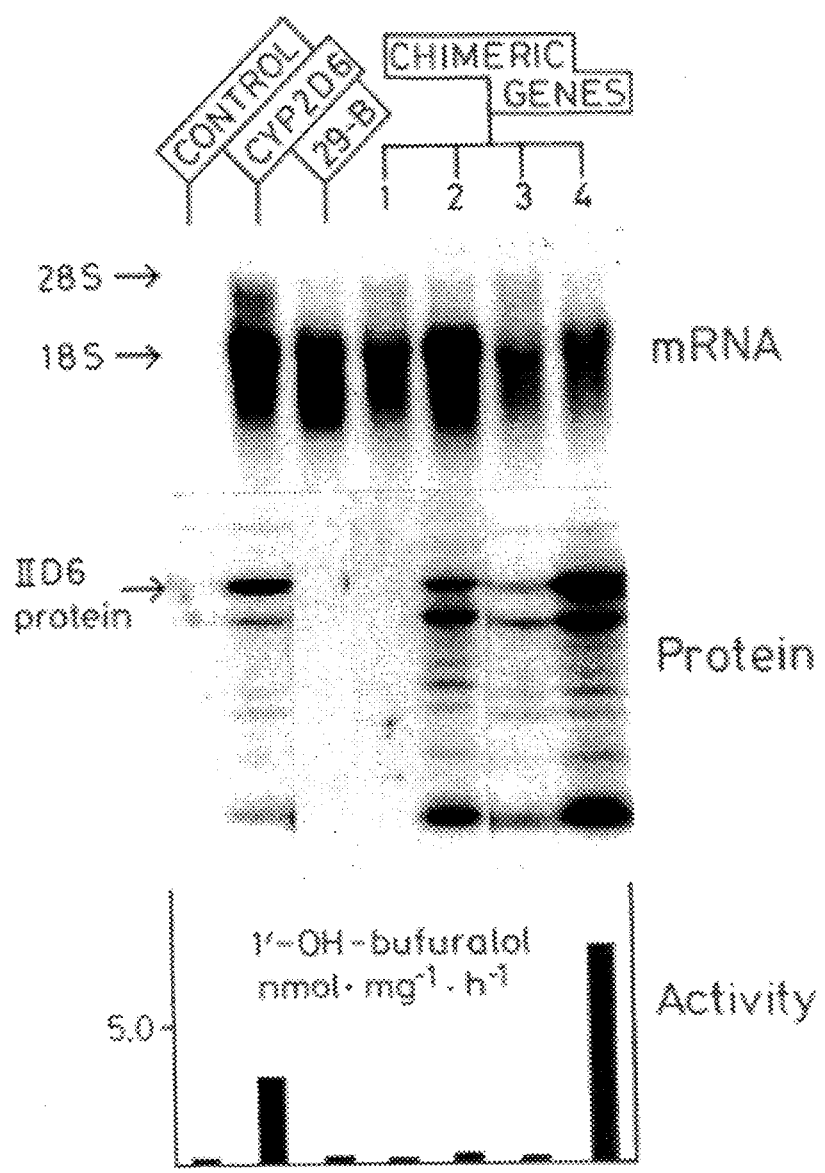

FIG. 6B, Northern blot (mRNA), Western blot (protein) and bufuralol 1'-hydroxylation of COS-1 cell extracts 66 h after transfection with the DNA constructs 1–4, the intact wild-type (CYP2D6) and the mutant (29-B) gene. Control, mock-transfected cells.

Figure 7A:
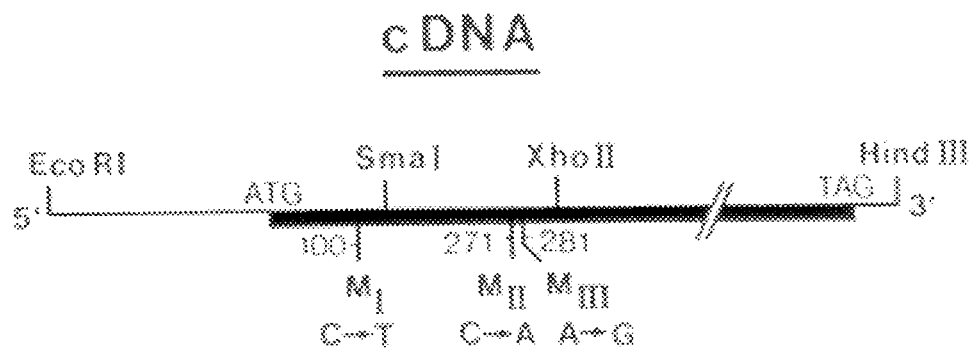
Figure 7B:
Figure 7C:
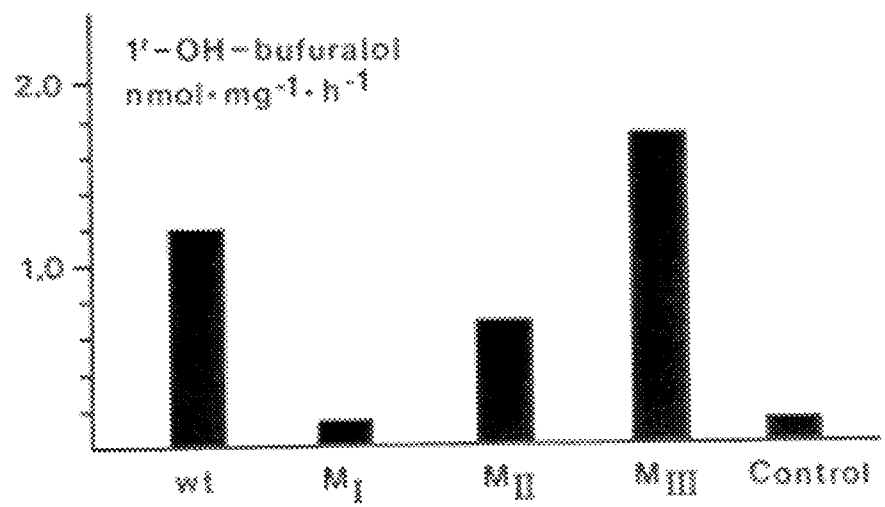

FIG. 7 shows the expression of single mutations of exon 1 (MI) and exon 2 (MII, MIII) of the CYP2D6 gene.

The mutations indicated in the top panel were introduced into the wild-type IID6-cDNA, transiently expressed in COS-1 cells and the expressed protein analysed by Western blotting and bufuralol 1'-hydroxylation activity as described below in Example 1.

Figure 8A:
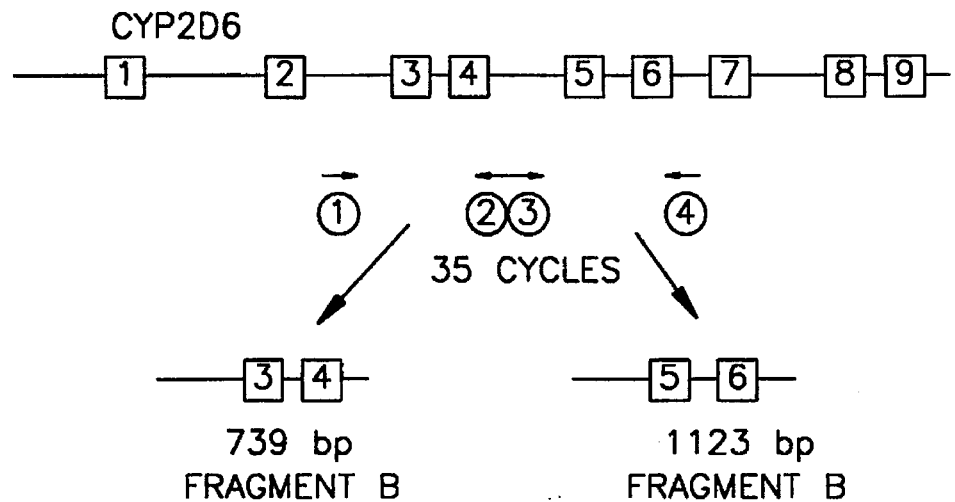
Figure 8B:
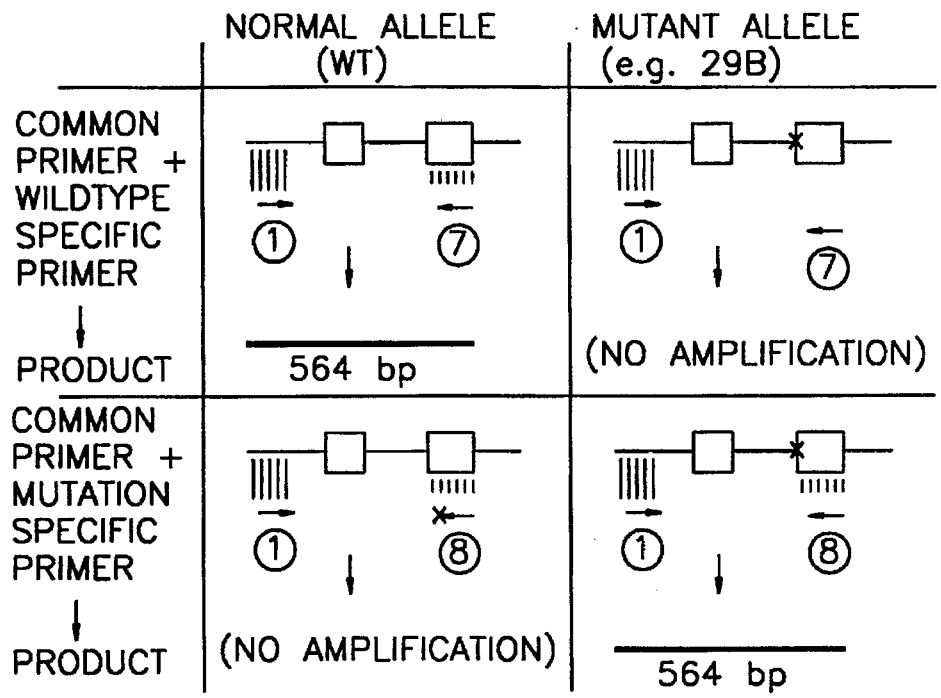

FIGS. 8A and 8B demonstrate the principle of allele-specific amplification.

FIG. 8A: Primer 1 to 4 are complementary to intronic sequences of the CYP2D6 gene. They are designed in order to exclude amplification from CYP2D7 or CYP2D8 (FIG. 1). The primer pair 1/2 yields the 739bp fragment B; the primer pair 3/4 the 1123bp fragment A.

FIG. 8B: One µl of the product of the first PCR is used in the second, allele specific PCR. The splice site mutation of the 29-B allele serves as the example, but the same principle is valid for the frame shift mutation of the 29-A allele. The "common primer" is primer 1, already used in the first-reaction. The two specific primers used are complementary to the sequence at the intron 3-exon 4 junction. The "wild-type specific primer" 7 generates an amplification product from template DNA without the splice site mutation, whereas the "mutation-specific primer" 8 binds only to the complementary sequence of the 29-B allele.

Figure 9:
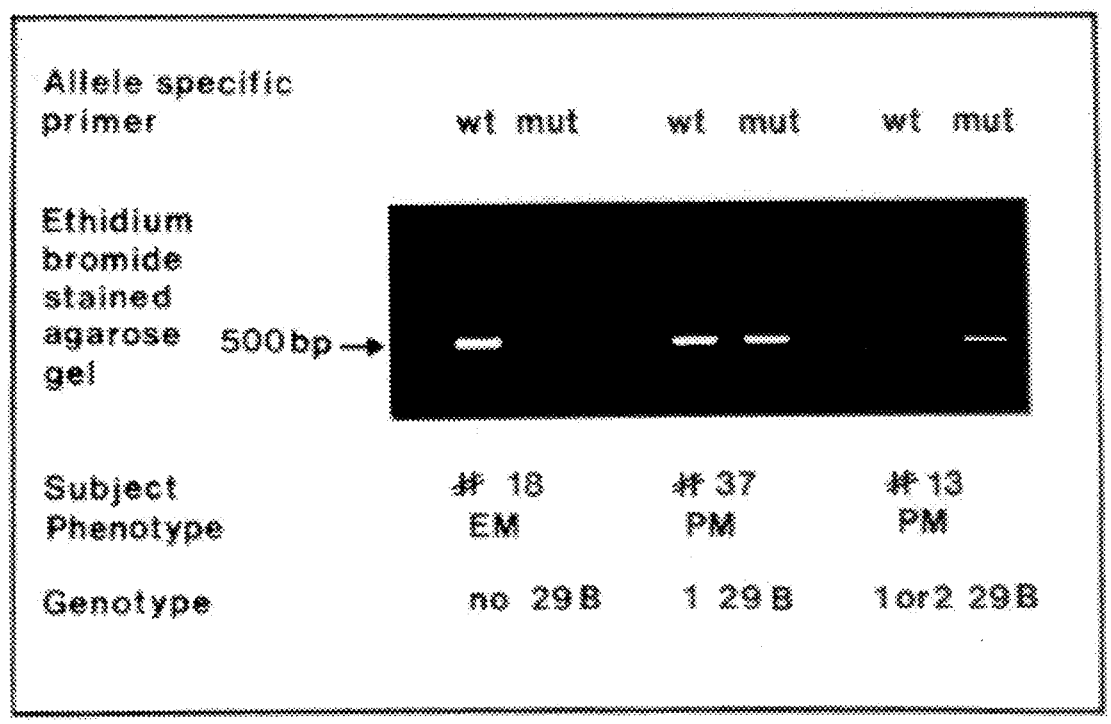

FIG. 9 shows the allele specific PCR amplification products of three individuals.

The three possible results are exemplified by the three subjects. Subject #18, with EM phenotype and a 29/29 kb XbaI RFLP pattern has no 29-B allele with a splice-site mutation. Subject #13 (PM, 29/29 kb XbaI), has one or two 29-B alleles and no allele with a normal splice- site, designated here as "wt". Subject #37 (PM, 29/29 kb XbaI), has one allele with a normal splice site (wt) and one allele with a mutated splice site (29-B).

Figure 10A:
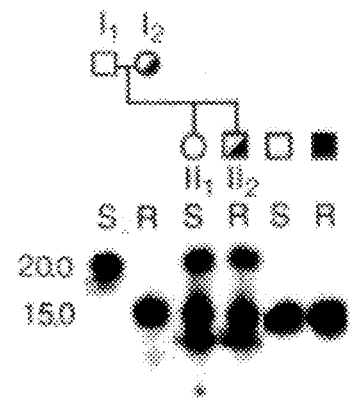
Figure 10B:
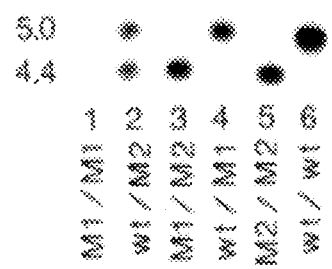

FIGS. 10A and 10B show the identification of the two mutant NAT2 alleles M1 and M2 by RFLP analysis and sequence determination of cloned mutants.

FIG. 10A KpnI patterns of a two-generation family (lanes 1–4) and of DNAs of two further individuals. Genomic DNAs (5 µg) were digested with the restriction enzyme KpnI, electrophoresed on 0.5% agarose gels and hybridized with radiolabeled NAT2 after transfer to a nylon membrane. Hybridization and washes were performed as described in the art, e.g. by Sambrook, Fritsch and Maniatis in "Molecular Cloning, a Laboratory Manual" (Cold Spring Harbor Laboratory Press [1982]). Phenotypes (R=rapid, S=slow acetylator) are given above each lane; numbers represent size of bands in kb.

FIG. 10B Nucleotide and amino acid changes in M1 and M2, as compared to the wild-type (wt) gene; nucleotide numbering refers to the coding exon (pos. 1=A in initiator ATG), as described by Blum et al. in DNA and Cell Biology 9, 193–203 (1990).

Figure 11:

FIG. 11 shows the allele specific amplification by PCR for the three mutations associated with the slow acetylator phenotype. The explanations of the bands visible in the lanes 1–6 are given in Example 5 below.

SUMMARY OF THE INVENTION

The present invention provides methods for the detection of normal and mutant genes coding for drug metabolizing enzymes which allow the phenotyping of poor (or slow) metabolizers mentioned above.

The invention also provides specific primers for the detection of the normal and mutated genes coding for drug metabolizing enzymes.

The invention further provides a method for detection of mutations of genes coding for drug metabolizing enzymes in a sample comprising a) amplifying a nucleic acid sequence of allelic forms of said gene with a wt-or mutation specific primer and a suitable gene specific primer
b) detecting the amplified products of step a).

DETAILED DESCRIPTION OF THE INVENTION AND PREFERRED EMBODIMENTS

The methods of the present invention use the polymerase chain reaction (PCR) as a source for selective amplification of DNA-fragments. This method is described in U.S. Pat. Nos. 4,683,195 and 4,683,202. The polymerase chain reaction is a procedure in which DNA is specifically amplified by multiple primer extension synthesis of complementary strands (Saiki et al., Science 230, 1350–1354 [1985] and 239, 487–491 [1988]).

The PCR product, amplified up to $10^6$–$10^7$ fold, is a DNA fragment of discrete size (ampiicon) which can be detected by gel electrophoresis, or by other means as described herein. Briefly, PCR involves the preparation of short oligonucleotide primers which correspond to opposing ends of a known "target" sequence which one intends to amplify and subsequently detect. In this procedure, DNA or RNA is extracted from cells, tissues, body fluids and the like. The nucleic acid is denatured and the oligonucleotide primers are added in molar excess, along with dNTPs (deoxyribonucleotide triphosphates) and a DNA polymerase enzyme, such as preferably heat stable Taq polymerase. This enzyme and its use is described in European Patent Application Publ. No. 258 017. Upon subsequent heat denaturing, cooling to allow annealing to primers, and primer extension by DNA polymerase, two "long products", which begin with the respective primers, are produced, complementary to the two original strands. This procedure is repeated and after a second cycle two original strands, two long products from cycle 1, two new "long products" and two "short products" are produced. The length of these short products (ampiicons) is equal to the number of nucleotides between and including both primers. With additional cycles, additional "long products" are produced, increasing in a linear fashion with each cycle. However, the generation of ampiicons increases at an exponential rate with each cycle and by means of this amplification the detection of extremely small quantities of DNA is enabled.

Any source of nucleic acids, in purified or nonpurified form, can be utilized as the starting nucleic acid or acids, provided it contains or is suspected of containing the specific nucleic acid sequence desired. Thus, the process may employ, for example, DNA or RNA, including messenger RNA, which DNA or RNA may be single stranded or double stranded. In addition, a DNA RNA hybrid which contains one strand of each may be utilized. A mixture of any of these nucleic acids may also be employed, or the nucleic acid produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the cytochrome P450 gene contained in whole human DNA. In fact, PCR amplification of DNA from single hairroots, buccal epithelial cells, blood spots or urinary sediments (Gasparine et al., N. Engl. J. Med. 320, 809 [1989]; Eisenstein, N. Engl. J. Med. 322, 178–183 [1990]) has been reported.

The great advantage of this approach for detection of PMs is that no probe drug has to be administered, no urine has to be collected and there is no interference with concurrent drug treatment which limits the usual phenotyping procedure (Brøsen et al., Eur. J. Clin. Pharmac. 36, 537–547 [1989]). Therefore, genotyping by the described procedure is an attractive and less ambiguous alternative to phenotyping by the urinary metabolic ratio.

The use of PCR for amplification of selected gene fragments of the CYP2D6 gene or mutant alleles thereof which are finally responsible for the debrisoquine phenotype, is exemplified in Examples 2 and 3 below. The two reactions involve, as already described before, as a first step amplification of the coding gene without selecting any mutant variants. Parts of these variant alleles are selectively amplified in the second reaction and then detected.

Allele-specific amplification in principle is possible by a single PCR reaction instead of the two consecutive reactions if no closely related genes have to be preselected in a prior step.

The present invention further provides primers for amplification of a nucleic acid sequence of alleles of genes coding for drug metabolizing enzymes to detect mutated and wt alleles, characterized in that primers have a length of about 10 to 50 bases and contain at the 3' end at least one base complementary to the mutation or to the wt sequence at the corresponding position and the remaining bases in the 5' direction being substantially complementary either to the sense or to the antisense strand of said gene. Preferably these primers are 10–25 bases in length.

Definitions of the terms Used in the specification and claims:

Drug metabolizing enzyme:

a protein, whose amino acid sequence has its origin in the nucleotide sequence of genes for drug metabolizing enzymes. These may be detected in the genome of mammalian individuals, e.g. humans, which are possessing these genes.

Nucleotide:

a subunit of a nucleic acid consisting of a phosphate group, a 5' carbon sugar and a nitrogen containing base. In RNA, the 5' carbon sugar is ribose. In DNA, it is a 2-deoxyribose. The term also includes analogs of such subunits.

Nucleotide polymer or oligonucleotide:

at least two nucleotides linked to each other by phosphodiester bonds. The term comprises primers, probes, nucleic acids fragments in labeled or unlabeled form.

Nucleic acid probe:

a single stranded nucleic acid sequence that will combine with a complementary single stranded target nucleic acid sequence to form a double-stranded molecule (hybrid) usually for subsequent detection. A nucleic acid probe may be an oligonucleotide or a nucleotide polymer.

Primer:

refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an inducing agent such as a DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact length of the primers will depend on many factors, including temperature, source of primer and use of the method. For example, for diagnostics applications, depending on the complexity of the target sequence, the oligonucleotide primer typically contains 15–25 or more nucleotides, although it may contain fewer nucleotides. For other applications, the oligonucleotide primer is typically shorter, e.g. 7–15 nucleotides. Such short primer molecules generally require cooler temperatures to form sufficiently stable hybrid complexes with the template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand.

A selected primer sequence is in principle also useful for the construction of a probe. Therefore, wherein a primer is mentioned, the corresponding possible application as a probe is incorporated.

Hybridization:

the process by which two complementary strands of nucleic acids combine to form double stranded molecules (hybrids).

Complementarity:

a property conferred by the base sequence of a single strand of DNA or RNA which may form a hybrid or double stranded DNA:DNA, RNA:RNA or DNA:RNA complex through hydrogen bonding between Watson-Crick base pairs on the respective strands. Adenine (A) usually complements thymine (T) or Uracil (U), while guanine (G) usually complements cytosine (C).

Primer Specificity:

characteristic of a primer which describes its ability to distinguish between target and nontarget sequences. Dependent on sequence and assay conditions. Primer specificity may be absolute (i.e. primer is able to distinguish between the target oligonucleotide and any nontarget oligonucleotide). The same is valid for a probe.

Restriction fragment length polymorphism (RFLP)

refers to the differences in DNA nucleotide sequences which produce different restriction endonuclease patterns. These patterns may change if mutations within the specific nucleotide sequence, recognized by a restriction enzyme, occurred.

Gene refers to a segment of DNA coding for the production of an RNA which leads to a protein molecule as the final product. It includes both the transcribed region and any sequences upstream and/or downstream responsible for its correct and regulated expression. Fragments comprising parts of this DNA are also included in this term. Different allelic forms of a gene are also included in this term.

PCR-technology shall mean polymerase chain reaction (PCR) technologies including but not limited to the nucleic acid amplification process covered by U.S. Pat. Nos. 4,683,195 and 4,683,202.

Polymorphism refers to the simultaneous occurence in the population of genomes (individuals) showing allelic variations and seen either on alleles producing different phenotypes or in changes in the DNA, affecting the restriction pattern caused by restriction enzymes.

Allele an allele consists of a segment of deoxyribonucleic acid (DNA) which comprises all the information needed to become expressed as a polypeptide chain. Thus, alleles differing in nucleotide sequences may give rise to different polypeptide chains or fail to make the protein. However, identical polypeptide chains may be derived from different alleles provided the nucleotide sequence differences are "silent" at the level of translation. Moreover, nucleotide sequence differences between alleles will not affect the polypeptide chain sequences provided the differences occur in introns or in untranslated portions of the exons. Consequently, alleles recognized as such at the DNA level may not emerge as alleles but as products of the same gene at the protein level. Allelic genes, although similar, differ from each other but occupy identical positions in the genome or at least chromosome. Due to the diploid character of the mammalian genome including the human ones, an individual can only express two alleles at the two given chromosomal loci. However, the entire population may express a large number of alleles at such a locus. Two identical alleles resulting in a homozygous, two different alleles in a heterozygous carrier of genetic information.

In one embodiment of this method, prior to the wt-or mutation-specific amplification step a), specific amplification of parts of the gene itself in a region containing the mutations is performed. This prevents the amplification of homologous sequences in related pseudogenes which may contain the same mutations and which amplification may result in false positives.

A preferred method for detecting poor metabolizers of the debrisoquine phenotype comprising the following steps:

a) amplifying a 739bp fragment of the CYP2D6 gene with primers comprising the sequences:

| 5' ATTTCCCAGCTGGAATCC 3' | SEQ ID NO:1 |
| and | |
| 5' GAGACTCCTCGGTCTCTC 3' | SEQ ID NO:2 | b) amplifying a small amount of the product of step a) with primers comprising the sequences:

| 5' ATTTCCCAGCTGGAATCC 3' | SEQ ID NO:1 |
| and | |
| 5' CGAAAGGGGCGTCC 3' | SEQ ID NO:3 | to obtain a 564bp fragment of the 29-wt and 29-A allele if contained in the sample.

c) amplifying another small amount of the product of step a) with primers comprising the sequences

| 5' ATTTCCCAGCTGGAATCC 3' | SEQ ID NO:1 |
| and | |
| 5' CGAAAGGGGCGTCT 3' | SEQ ID NO:4 | to obtain the 564bp fragment of the 29-B allele if contained in the sample.

d) detecting the occurrence of the reaction product of reactions b) and c).

Another preferred method for detecting poor metabolizers of the debrisoquine phenotype comprises the following steps:

a) amplifying a 1123bp fragment of the CYP2D6 gene with primers comprising the sequences

| 5' GCGGAGCGAGAGACCGAGGA 3' | SEQ ID NO:5 |
| and | |
| 5' CCGGCCCTGACACTCCTTCT 3' | SEQ ID NO:6 | b) amplifying a small amount of the product step a) with primers comprising the sequences

| 5' CCGGCCCTGACACTCCTTCT 3' | SEQ ID NO:6 |
| and | |
| 5' GCTAACTGAGCACA 3' | SEQ ID NO:7 | to obtain a 588bp fragment of the 29-wt and 29-Ballele if contained in the sample.

c) amplifying a small amount of the product of step a) with primers comprising the sequences

| 5' CCGGCCCTGACACTCCTTCT 3' | SEQ ID NO:6 |
| and | |
| 5' GCTAACTGAGCACG 3' | SEQ ID NO:8 | to obtain a 588bp fragment of the 29-A allele if contained in the sample d) detecting the absence or presence of products of steps b) and c).

A method for detecting poor metabolizers of the acetylation phenotype is possible by RFLP analysis which results in identification of mutant alleles M1, M2 and M3.

To identify mutant alleles restriction fragment analysis was performed on genomic DNA samples from 25 healthy individuals whose acetylator phenotype had been established by measuring the acetylated metabolite of caffeine in urine (Grant et al., Br. J. Clin. Pharmacol. 17,459–464 [1984]), and on DNA from 33 human liver samples with known NAT2 enzyme activity measured with the substrate sulfamethazine (SMZ; Grant et al., J. Clin. Invest. 85, 968–972 [1990]). Hybridization and wash conditions were chosen so that NAT2- specific signals were 10–50 fold stronger than signals derived from the two related human genes, NAT1 and NATP, which share 87% and 79% nucleotide identity with NAT2. Restriction fragment length polymorphisms generated by MspI and KpnI segregated with acetylator phenotype; for simplicity and because MspI detected only one mutant allele (M1), only KpnI RFLPs are shown in FIG. 10a. The patterns in lanes 1–4 show segregation of NAT2-specific fragments in a two-generation family. The wt allele thus was characterized by two bands of 15kb and 5kb, whereas mutant allele M1 was reflected by a single band of 20kb (lane 1), and mutant allele M2 by two fragments of 15kb and 4.4kb. Examples of DNA individuals homozygous for M2 and for wt, respectively, are shown in lanes 5 and 6 of FIG. 10a.

In both M1 and M2 a point mutation causing a single amino acid change in the deduced protein sequence was combined with an additional silent base substitution (FIG. 10b). The silent mutation in M1 alters the recognition sequence for the restriction enzyme KpnI, explaining the observed RFLP (FIG. 10a).

Another preferred method of the present invention for detecting (genotyping) poor metabolizing individuals having the slow acetylation phenotype is as follows:

(a) amplifying a 568bp fragment of the NAT2 gene in a sample with the putative mutant M1 and/or the wild-type allele using primers comprising the sequence

| 5' AAT TAG TCA CAC GAG GA 3' | SEQ ID NO:9 |
| 5' CTG ATT TGG TCC AG 3' | SEQ ID NO:10 |
| for the wt allele | | and primers comprising the sequence

| 5' AAT TAG TCA CAC GAG GA 3' | SEQ ID NO:9 |
| 5' CTG ATT TGG TCC AA 3' | SEQ ID NO:11 |
| for the mutant M1 allele, | |

(b) amplifying a 565bp fragment of the NAT2 gene in a sample with the putative mutant M2 and/or the wild-type allele using primers comprising the sequence

| 5' TCT AGC ATG AAT CAC TCT GC 3' | SEQ ID NO:12 |
| 5' TTT ACG CTT GAA CCT CG 3' | SEQ ID NO:13 |
| for the wt allele | | and primers comprising the sequence

| 5' TCT AGC ATG AAT CAC TCT GC 3' | SEQ ID NO:12 |
| 5' TTT ACG CTT GAA CCT CA 3' | SEQ ID NO:14 |
| for the mutant M2 allele. | |

(c) amplifying a 944bp fragment of the NAT2 gene in a sample with the putative mutant M3 and/or the wild-type allele using primers comprising the sequence

| 5' AAT TAG TCA CAC GAG GA 3' | SEQ ID NO:9 |

-continued

| | |
|---|---|
| 5' AAT AGT AAG GGA TC 3' | SEQ ID NO:15 |
| for the wild-type allele | | and primers comprising the sequence

| | |
|---|---|
| 5' AAT TAG TCA CAC GAG GA 3' | SEQ ID NO:9 |
| 5' AAT AGT AAG GGA TT 3' | SEQ ID NO:16 |
| for the mutant M3 allele. | |

(d) detecting which of the reactions described above result in amplified fragments allowing the determination of the genotype of the analysed person.

Only one step is required in the NAT2 case because the primers

| | |
|---|---|
| 5' AAT TAG TCA CAC GAG GA 3' | SEQ ID NO:9 |
| and | |
| TCT AGC ATG AAT CAC TCT GC | SEQ ID NO:12 | amplify only the NAT2 gene and no related pseudogenes. Nevertheless, the two-step-procedure including selective gene amplification prior to the selective allele amplification as shown in the case of the debrisoquine polymorphism may also be employed for the NAT2 gene in the acetylation polymorphism.

It is understood that the sample used in these different amplification reactions is of the same genetic origin (e.g. the same person). The sample may be prepared and subdivided once for all amplifications or the sample is prepared from different sources (e.g. hair, skin, liver etc.) which are finally of the same genetic origin. Further details of the amplification are given in Example 5 below.

This DNA assay permits the prediction of the acetylator phenotype in over 95% of individuals tested and requires only a small sample of DNA, which may be derived from leukocytes, single hair roots, buccal epithelia, or any other tissue.

The sequences of the mutant NAT2 alleles were obtained with methods known in the art. The methods employed were similar to those used in the genetic analysis of the alleles in the debrisoquine polymorphism which are extensively described in Example 1 below. Briefly, the cloning and sequencing of mutant NAT2 alleles of the acetylation polymorphism was as follows:

Mutant allele M1 was isolated from a genomic library constructed in λEMBL3, using DNA from a heterozygous wt/M1 individual. A cDNA encoding the rabbit NAT2 enzyme protein described by Blum et al. in *Nucl. Acid. Res.* 17, 3589 (1989) was used for screening. For sequence analysis of M1 the 1.9kb EcoRI fragments containing the single coding exon of NAT2 were isolated from 12 positive λEMBL3 clones and subcloned into pBluescript (Stratagene). Relevant methods used for cloning of normal and mutant NAT genes are also described by Blum et al. in DNA and *Cell Biology* 9, 193–203 (1990). M2 was Blum et al. in *DNA and Cell Biology* 9, 193–203 (1990). M2 was cloned from DNA of a homozygous M2/M2 individual by screening of a λgt10 library constructed from EcoRI digested genomic DNA following size selection (1.6–2.1kb) on a 1% agarose gel. The 1.9kb EcoRI fragment containing wild-type (wt) NAT2 coding exon was used as hybridization probe and the inserts of positive phages were also subcloned into pBluescript. Sequences of M1 and M2 were determined using the dideoxy chain termination method of Sanger et al., described in *Proc. Natl. Acad. Sci. USA*, 74, 5463–5467 (1977) and Sequenase (USB). The mutations including the consequent amino acid changes are shown in FIG. 10b.

The sequence of M3 has been published in another laboratory (Ohsako et al., *Biol. Chem.* 265, 4630–4634 [1990]). It is a rare case of the slow acetylation phenotype in Caucasions.

In a preferred embodiment the primers for amplification of nucleic acid sequences of alleles of the CYP2D6 gene have at their 3' end a base which is complementary to base Nos. 1062, 1072, 1085, 1749, 1934, 2637 or 4268 of the wt or mutated CYP2D6 gene sequence coding for the P450IID6 enzyme.

Most preferred are primers comprising a sequence selected from the group consisting of

| | |
|---|---|
| 5' CGAAAGGGGCGTCC 3' | SEQ ID NO:3 |
| 5' CGAAAGGGGCGTCT 3' | SEQ ID NO:4 |
| 5' GCTAACTGAGCACA 3' | SEQ ID NO:7 |
| 5' GCTAACTGAGCACG 3'. | SEQ ID NO:8 |

The invention further provides primers for amplification of a nucleic acid sequence of alleles or the NAT2 gene coding for the N-acetyltransferase. Preferably these primers have at their 3' end bases complementary to base No. 282, 341, 481, 590 or 857 of the wt or mutated NAT2 gene sequence.

Most preferred are primers comprising a sequence selected from the group consisting of

| | |
|---|---|
| 5' CTG ATT TGG TCC AG 3' | SEQ ID NO:10 |
| 5' CTG ATT TGG TCC AA 3' | SEQ ID NO:11 |
| 5' AAT AGT AAG GGA TC 3' | SEQ ID NO:15 |
| 5' AAT AGT AAG GGA TT 3' | SEQ ID NO:16 |
| 5' TTT ACG CTT GAA CCT CG 3' | SEQ ID NO:13 |
| 5' TTT ACG CTT GAA CCT CA 3'. | SEQ ID NO:14 |

The invention further provides primers for selective amplification of nucleic acid sequences of regions which contain mutations of genes coding for drug metabolizing enzymes characterized in that said primers have a length of about 10 to 50 bases and being substantially complementary to the sense or antisense strand of said gene in said region to allow selective amplification of parts of the gene itself including mutations thereof and to prevent amplification of homologous sequences in related pseudogenes.

Preferably the primers for selective amplification of nucleic acid sequences of the CYP2D6 gene comprise a sequence selected from the group consisting of

| | |
|---|---|
| 5' ATTTCCCAGCTGGAATCC 3' | SEQ ID NO:1 |
| 5' GAGACTCCTCGGTCTCTC 3' | SEQ ID NO:2 |
| 5' GCGGAGCGAGAGACCGAGGA 3' | SEQ ID NO:5 |
| 5' CCGGCCCTGACACTCCTTCT 3' | SEQ ID NO:6 |

Preferably, primers for selective amplification of nucleic acid sequences of the NAT2 gene comprise the following sequences

| | |
|---|---|
| 5' AAT TAG TCA CAC GAG GA 3' | SEQ ID NO:9 |
| 5' TCT AGC ATG AAT CAC TCT GC 3' | SEQ ID NO:12 |

These primers can be used as suitable gene specific primers mentioned in the amplification method for the detection of mutations in genes coding for drug metabolizing enzymes described above. Such primers are designed to allow specific amplification of a nucleic acid sequence of a gene coding for drug metabolizing enzymes including any alleles thereof. Therefore, these primers serve a twofold purpose. Using two of these gene specific primers amplification of a nucleotide sequence of a gene coding for drug metabolizing enzymes is possible. With this amplification primers a preselection of the gene is possible thereby separating it from possible closely related pseudogenes but wherein the mutations in the amplified nucleotide sequence need further characterisation because the amplified nucleotide sequence then additionally may consist of different sequences resulting from different mutations within different alleles of the gene in the amplified region of the gene. These primers alone are not able to amplify specific alleles of this gene. This is only possible when using one of them in combination with the allele specific primers described above. If separation of closely related pseudogenes is not necessary these gene specific primers may be used directly in connection with allele specific primers to amplify and detect specifically the wt-and mutated alleles of the genes coding for drug metabolizing enzymes. Otherwise, the gene specific primers can be used once more after the gene amplification in the allele specific amplification step together with the allele specific primers. It is also possible to use new gene specific primers in connection with the allele specific primers for the allele specific amplification.

Probes, preferably in a labeled form are directly used for detection of a target nucleic acid sequence in a sample, whereas a primer is used to produce a greater amount of the target DNA followed by direct detection of the amplified product, preferably by gel electrophoresis. A labeled probe for detection may additionally be used after amplification. Another possibility is the use of labeled primers or labeled nucleoside triphosphates in the amplification reaction since these primers and nucleotides are incorporated into the amplified nucleic acid sequence, facilitating their detection later on. Selected oligonucleotide probes and primers may be labeled by any of several well-known methods. Useful labels include radioisotopes as well as non-radioactive reporting groups. Isotopic labels include $^3H$, $^{35}S$, $^{32}P$, $^{125}I$, Cobalt and $^{14}C$. Most methods of isotopic labeling involve the use of enzymes and include the known methods of nick-translation, end labeling, second strand synthesis and reverse transcription. When using radio-labeled probes, hybridization can be detected by autoradiography, scintillation counting or gamma counting. The detection method selected will depend upon the hybridization conditions and the particular radioisotope used for labeling.

Non-isotopic materials can also be used for labeling and may be introduced by the incorporation of modified nucleotides through the use of enzymes or by chemical modification of the probe, for example by the use of non-nucleotide linker groups. Non-isotopic labels include fluorescent molecules, chemiluminescent molecules, enzymes, cofactors, enzyme substrates, haptens or other ligands.

The primers of the present invention overcome the problem of detection sensitivity in conventional probe based systems. If only small amounts of the target sequence in a sample are available, probes may fail to detect them.

The primers of the present invention are usable without further modifications and are easily synthesized on a DNA-synthesizer by any of several well-known methods, e.g. including automated solid-phase chemical synthesis using β-cyanoethyl phosphoramidite precursors. In general, the synthesis can be carried out both in liquid phase and on a solid phase, as described, for example, in Science 230, 281 (1985), Chimia 41, 302 or in "Oligonucleotide Synthesis: A practical Approach", IRL Press, Oxford, UK, M. J. Gait, Ed. (1984).

Detection of amplified target sequences is easy due to the large amount produced by the polymerase chain reaction. Gel electrophoreses of the fragments obtained followed by visualization using UV-shadowing or staining methods known in the art is preferred allowing analysis of the presence and length of the expected target oligonucleotides (Maniatis et al., A laboratory manual, Cold Spring Harbor Laboratory, 1982).

Genes coding for different proteins usually are selectively amplified since the corresponding oligonucleotide sequences are different enough from each other to allow the construction of two gene selective amplification primers.

Discrimination between wild-type and mutant alleles of a gene is more difficult. This is achieved by placing the mutant base (or bases) at the 3' end of the primer. Under appropriate amplification conditions only the allelic sequence with the complementary primer possessing the correct Watson-Crick base pairing at the 3' end of the primer will be amplified.

In the same manner as described hereinbefore further sequenced genes for drug metabolizing enzymes can be detected and analysed.

The methods of the present invention can be carried out in test kits comprising in combination the following reagents:

Primers for gene specific amplification. Primers for allele specific amplification. These primers will typically be in separate containers in the kit. The kit may also include a denaturation reagent for denaturing the analyte, hybridization buffers, enzyme and enzyme substrates, negative and positive controls and written instructions for carrying out the assay.

Example 1

A) Characterization of PM-Individuals

The leukocyte DNA of three individuals of PM-phenotype was selected from a collection of DNA samples for population and family studies (Skoda et al., Proc. Natl. Sci. USA 85, 5240–5243 [1988]). The three subjects indexed as PM1 (ZICL), PM2 (KABI) and PM3 (B07) were identified as PMs by phenotyping with either debrisoquine (Meier et al., Gastroenterology 85, 682–692 [1983]) or sparteine (Eichelbaum et al., Xenobiotica 16, 465–481 [19861]). The urinary debrisoquine/4-OH-debrisoquine metabolic ratio was 332 and 55 for PM1 and PM2, respectively. PM3 was identified with the urinary sparteine/dehydrosparteine metabolism ratio, which was 250. These PMs were selected because they are of the XbaI 29 kb/29 kb genotype, which provides no information on the phenotype by restriction analysis. The sequence information of the wild-type CYP2D6 gene used for comparison was from a homozygous extensive metabolizer (EM) individual (EZA) described by Kimura et al. (Am. J. Hum. Gem 45, 889–904 [19891]). Southern blot analysis was performed as described (Skoda et al., supra).

B) Cloning and Sequencing of Mutant CYP2D6 Genes

The strategy of cloning was based on the information derived from Southern blots with BamHI, EcoRI and XbaI and the almost complete sequence of the area of the three genes CYP2D6, CAP2D7 and CYP2D8 isolated from extensive metabolizer DNA (Kimura et al., Am. J. Hum. Gen. 45, 889–904 [19891] and Skoda et al., supra). According to this, the 16 kb EcoRI fragment contains the CYP2D7 gene, which is located 5' of the normal CYP2D6. The 9.4 kb EcoRI fragment represents the CYP2D6 gene and the 8.5 kb fragment the CYP2D8 pseudogene. Genomic libraries were constructed from leukocyte DNA of each of the 3 PM-individuals. Since Southern blot analysis of their genomic DNA had the same EcoRI pattern as EMs it was assumed that their 16, 9.4 and 8.5 kb fragments contain the same CYP2D genes as DNA of the wild- type or homozygous extensive metabolizer. DNA was completely digested with EcoRI and inserted into the vector λgtWES (BRL). This vector can process 2–15 kb inserts. Because the 16 kb fragment is too long to be accepted by λgtWES, these libraries contain only the 9.4 and 8.5 kb fragments, corresponding to the CYP2D6 and CYP2D8 genes. The libraries were screened with two probes to ensure the identification of clones representing the CYP2D6 gene. Both probes were labeled with [$^{32}$P] by nick-translation. The first screening was done with the full length IID6-cDNA (Gonzalez et al., supra), which recognizes both the CYP2D6 and CYP2D8 clones. Therefore, an additional probe, a SacI 0.4 kb fragment (bp -717 to 305) was used and prepared from the genomic DNA of a homozygous extensive metabolizer. This fragment recognizes the 5' flanking region of both the CYP2D6 and CYP2D7 gene, but not the CYP2D8 gene. As the library only contains CYP2D8 and CYP2D6 genes, the second screening with this probe thus selects for CYP2D6. Two positive clones were isolated from the genomic libraries of each of the 3 PM individuals (FIG. 3). It was unknown at this time if the two clones are derived from the same allele. Four of these 6 clones (29-B, 29-B, 29-B', 29-A) were fully sequenced in all exons and intron-exon junctions. The remaining 2 clones ((29-B)(29-B)) were only partially sequenced as detailed below. The EcoRI fragments of the positive clones were digested with various restriction enzymes to smaller DNA fragments, these were subcloned into pUC19 and sequenced by the double strand dideoxy chain termination method (Sanger et al., *Proc. Natl. Sci. USA* 74, 5463–5467 [1977] and Hattori et al., *Analytical Biochemistry* 152, 232–238 [1986]), using universal and reverse primers as well as 18 synthesized oligonucleotides (20-mers) corresponding to the 5' and 3' part of each of the 9 exons and the intron-exon junctions.

PM1 and PM2: One clone of the two isolated from each PM- library was first sequenced in all exons and intron-exon junctions. It became clear that these two clones had identical mutations as well as an additional BamHI restriction site when compared to the wild-type CYP2D6 gene (FIG. 3, 4). They were designated 29-B. The second clone from each PM was sequenced only in two areas where mutations had been identified, namely the 3'-intron-exon junction of the 3rd intron and exon 2. The same mutations were again detected as well as the additional BamHI site present in both alides in PM1 and PM2, already evident in the genomic Southern blot analysis. It is of course unknown if the two clones are derived from the same allele or not.

The mutations of the 29-B allele are summarized in FIG. 4. They include 2 silent mutations (1085 C to G, 1749 G to C), 4 amino acid changes (188 C to T resulting in 34 Pro to Set, 1062 C to A resulting in 91 Leu to Met, 1072 A to G resulting in 94 His to Arg, 4268 G to C resulting in 486 Ser to Thr) and one nucleotide change (1934 G to A) at the 3' end of the 3rd intron. The G to A change at the last nucleotide of intron 3 found in all 29-B alleles is suspected to be the dominant cause for absent protein and function, because the consensus acceptor site sequence AG is conserved to 100% in numerous genes of human and other species examined (Ohshima et al., *J. Mol. Biol.,* 195, 247–259 [1987]). Point mutagenesis experiments support the concept that the "AG" consensus acceptor site sequence is a prerequisite for a normal splicing mechanism (Aebi et al., *Cell* 47, 555–565 [1986]). There was no difference in the size of the RNA in the Northern blots analysis of the COS- cells in which this mutation was expressed (FIG. 6B). The 29-B allele contains multiple additional mutations and may have more in the unsequenced introns. The sequence positions correspond to the published CYP2D6 sequence (Kimura et al., *Am. J. Hum. Gen.* 45, 889–904 [19891]).

PM3: With the knowledge of the additional BamHI site in the clones from PM1 and PM2, PM3 was selected to be studied because this poor metabolizer individual in his genomic Southern blot was heterozygous for this BamHI site. Both clones from PM3 were fully sequenced. One allele was identical to the mutant allele 29-B, except for the silent mutation (1749 G to C) in exon 3 and it therefore was designated 29-B'.

The other allele, which had no additional BamHI site, had one nucleotide deletion (2637 A) in the 5th exon resulting in a frame shift. This allele was designated 29-A (FIG. 3, 4).

C) Construction of Expression Clones

The construction of the full length expression clones is summarized in FIG. 5.

CYP2D6 wild-type: An AccI-KpnI fragment from the 3' part of CYP2D6 wild-type gene was blunt-ended by treatment with T4 DNA polymerase (BRL) and subcloned into pUC19 by using the HincII site in the correct orientation. The HincIIfragment of the same gene was subcloned into the SmaI site of the Bluescript vector (Promega) in the correct orientation. The EcoRI-BamHI fragment of the former clone was then replaced with that of the latter clone to construct a full length gene in pUC19. The resulting gene was excised by EcoRI and HindIII, and inserted into the pCMV expression vector (Andersson et at., *J. Biol. Chem.* 264, 8222–8229 [1989] and Thomson et al., *Proc. Natl. Acad. Sci. USA* 81,659–663 [1984]), using the same restriction sites.

CYP2D6 mutated genes (29-B allele): The EcoRI-KpnI fragment of the mutant 29-B gene was subcloned into pUC19 (BRL). This clone was digested by HindIII and SalI, blunt-ended by T4 DNA polymerase and ligated again in order to eliminate the AccI site in the vector. The HindIII site in the vector was maintained during this procedure. The HindII fragment of the mutated 29-B gene was then subcloned into the SmaI site of another pUC19 in the correct orientation and the EcoRI-BssHII fragment of the former clone was replaced with that of this clone. The engineered full length gene in pUC19 was further subcloned into pCMV using EcoRI and HindIII sites.

As shown in FIG. 6B, the CYP2D6 wild-type gene construct produced functional and immuno-reactive protein in COS-1 cells. The mutated 29-B gene on expression did not result in recognizable protein and no enzymatic activity could be demonstrated in transfected COS-1 cells (Example 1F). The mRNA was recognized by the IID6 cDNA in Northern blots (Example 1G) and had the same apparent size for both constructs (FIG. 6B).

D) Chimeric genes

Chimeric genes were assembled in pUC19 using combinations of the three parts (EcoRI-BssHII, 1.8 kb; BssHII-AccI, 0.8 kb; AccI-HindIII, 1.8 kb) of the constructed full length gene clones (FIG. 6A). The total length of the chimeric genes thus was 4.4 kb. The chimeric genes were inserted as described in Example 1C into pCMV using EcoRI and HindIII restriction sites.

Chimeric Genes Nos. 1 and 2. Because of the suspected importance of the mutation in the splice-site consensus sequence at the 3' and of the 3rd intron, we first constructed chimeric genes which would allow us to test the consequences of this mutation. The No. 1 chimeric gene includes the middle part of the mutated 29-B allele, and the 5' and 3' part of the wild-type gene (FIG. 6A). In the No. 2 construct, on the other hand, the middle part was derived from the wild-type gene, and the 5' and 3' part from the mutated 29-B allele. On expression (Example 1F, FIG. 6B), the No. 1 chimeric gene resulted in no recognizable protein and no enzyme activity, as with the entire 29-B gene. The size of the mRNA was identical to the 29-B and wild-type gene products (FIG. 6B). mRNA analysis was performed as described in Example 1G. The No. 2 chimeric gene apparently produced a similar amount of IID6 protein as the wild-type-IID6 gene, but no significant activity over COS-1 cell controls.

Chimeric Genes Nos. 3 and 4. To evaluate the effect of the amino acid changes in the 5' and 3' part of the 29-B allele, the No. 3 and 4 clones were constructed which include the 5' and 3' parts of the 29-B gene, each combined with the other two parts of the wild-type gene. The No. 3 clone produced an immunoreactive protein, but no activity, as did the No. 2 chimeric gene described above. Therefore, the three amino acid changes in the 5' part of the gene together or alone are capable of destroying the function of this protein (Example 1E). However, chimeric gene No. 4 conferred on expression the same or even higher activity as the wild-type gene. This indicates that the amino acid change (486 Ser to Thr) caused by the mutation in the 9th exon is not important for expression or activity. Western blot analysis (Example 1H) of the products of clones Nos. 2, 3 and 4 revealed several additional shorter bands some of which were also seen in the products of the wild-type gene (FIG. 6B, lane 2).

E) Point mutations in Exon 1 and 2: A full length human CYP2D6-cDNA was constructed by subcloning a 400bp EcoRI- SmaI fragment containing the first 140bp of the coding sequence and 260bp of the 5' untranslated region of a CYP2D6 wild-type genomic clone (Kimura et al., *Am. J. Hum. Gen.* 45, 889–904 [1989]) into a rat-human hybrid cDNA that was deleted of the corresponding part by cutting it with the same restriction enzyme. The same strategy was used to construct a cDNA containing only mutation 1 (MI, 188 C to T) by using a genomic clone of a 29-B allele. Mutation 2 (MII, 1062 C to A) and mutation 3 (MIII, 1072 A to G) were introduced into the wild-type cDNA by the polymerase chain reaction according to Kammann et al., *Nucleic Acids Res.* 17, 5404 [1989]), using two mutagenic primers (GGGTCACCATCGCCTCGCG SEQ ID NO:17 for MII, TCCTCGCCGCGGGTCACCA SEQ ID NO:18 for MIII). A unique XholI site was used to subclone the PCR generated fragments into the wild-type cDNA (FIG. 7). All constructs were sequenced as described in Example 1B to exclude PCR artifacts.

All three mutated cDNAs were expressed in COS-1 cells and resulted in immunoreactive protein (FIG. 7), but only the mutation in exon 1 (188 C to T, 34 Pro to Ser) abolished the activity of the expressed protein, the activity being as low as in mock-transfected control cells.

F) DNA Transfection of COS-1 Cells

Expression clones were transfected into COS-1 cells (Y. Gluzman, *Cell* 23, 175–182 [1981]) by the diethylaminoethyl (DEAE)-dextran method (Sompayrac et al., *Proc. Natl. Sci. USA* 78, 7575–7578 [1981]and Zuber et al. *Science* 234, 1258–1261 [1986]) with slight modifications. Sixteen hours before transfection, COS-1 cells were passaged from a confluent 100 mm culture dish to 4 dishes in Dulbecco's modified Eagle's medium (DMEM) containing 10% fetal calf serum (FCS). Transfection was performed by incubation of the cells for 2 h with DEAE-dextran (250 µg/ml; Pharmacia) and DNA (20 µg/plate) in serum-free DMEM, followed by an incubation for 3 h in DMEM containing 10% FCS and chloroquine (52 µg/ml; Sigma). The cells were harvested for analysis of IID6 protein and function after 66 h of incubation in DMEM with 10% FCS. For an assessment of IID6 function in intact cultured cells, (+)bufuralol (200 µM) was added to the cultures for the last 24 hours, and 1'-hydroxybufuralol analysed in the medium (Example 1I) (Zanger et al., *Proc. Natl. Acad. Sci USA* 85, 8256–8260 [1988]).

G) RNA Blot Analysis

Twenty µg of total RNA, which was isolated (M. Wilkinson, *Nucleic Acids Res.* 16, 10933 [1988]) from the transfected COS-1 cells, was size-fractioned by electrophoresis in 1.0% agarose-formaldehyde gels (Maniatis et al., *Molecular Cloning: A Laboratory Manual.* Cold Spring Harbor Laboratory, Cold Spring Harbor, N.Y. [1982]). The full length CYP2D6 cDNA, which was radio-labeled by the random priming method (Feinberg et al., *Anal. Biochem.* 132, 6–13 [1983], was used as the probe. Transfer of the RNA to a nylon membrane (Gene Screen Plus; Dupont, New England Nuclear) and hybridization with the radio-labeled probe were performed under the conditions recommended by Dupont.

H) Immunoblot Analysis SDS-PAGE of COS-1 cellhomogenates (protein 50–100 µg/lane) was performed in a 10% polyacrylamide gel, the proteins were transferred to nitrocellulose, exposed to the monoclonal antibody 114/2 and subsequently to rabbit antimouse IgG. The bound IgG was visualized by autoradiography after incubation with $^{125}$I-protein A (Zanger et al., *Proc. Natl. Acad. Sci. USA* 85, 8256–8260 [1988]).

I) Assay of Bufuralol-1'-Hydroxylation

Bufuralol 1'-hydroxylation assays were done as described for microsomal fractions by Zanger et al. (*Biochemistry* 27, 5447–5454, [1988]) in the presence of NADPH and $O_2$. COS-1 cells were harvested in PBS, the suspension centrifuged at 1000 g for 3 min, the pellet resuspended in sodium phosphate buffer, pH 7.4, sonicated 3 times for 10 seconds at 4° C. and the assay performed with 350 µg protein. Substrate concentration of (+)-bufuralol was 500 µM.

Example 2

CYP2D6-Specific Amplification

The CYP2D gene cluster on chromosome 22 (FIG. 1A) contains three closely related genes, the functional CYP2D6 gene coding for P450IID6 and two nonfunctional genes CYP2D7 and CYP2D8P (Kimura et al., infra). Some of the mutations of the CYP2D6 (D6) gene in the defective 29-A and 29-B alleles are also present in CYP2D7 (D7) and CYP2DSP (DS) genes of the wild-type allele.

In order to exclude "false positive" detection of mutations in pseudogenes, the DNA fragments of the D6 gene containing mutations of the 29-A and 29-B allele were specifically amplified. This was achieved by 18bp or 20bp oligonucleotide primers complementary to CYP2D6-unique intronic sequences on both sides of the mutations of interest (FIG. 8A). These primers are complementary to the following stretches of the CYP2D6-sequence (the numbering corresponds to that used by Kimura et al., *Am. J. Hum. Genet.* 45, 889–904 [1989]): Primer 1 (ATTTCCCAGCTGGAATCC) SEQ ID NO: 1 from 1385 to 1402; primer 2 (GAGACTCCTCGGTCTCTC) SEQ ID NO:2 from 2105 to 2122; primer 3 (GCGGAGCGAGAGACCGAGGA) SEQ ID NO:5 from 2098 to 2117; and primer 4 (CCGGCCCTGACACTCCTTCT) SEQ ID NO:6 from 3181 to 3200.

The first PCR reaction (CYP2D6-specific amplification) carried out for specific amplification of CYP2D6-specific fragments yielded a 739bp fragment (fragment B) with the primer pair 1/2 and a 1123bp fragment (fragment A) with the primer pair 3/4 (FIG. 3A). Fragment B contained part of intron 2, exon 3, intron 3, exon 4 and part of intron 4. Fragment A consisted of part of intron 4, exon 5, intron 5, exon 6 and part of intron 6. No fragments were amplified from the control samples with DNA from an individual having the 11.5/11.5 kb XbaI genotype. Leukocyte DNA initially was from the individuals described in Example 1A. Their phenotype was determined with debrisoquine, sparteine or dextromethorphan as described in Example 1A. The oligonucleotide primers were synthesized on an Applied Biosystems DNA synthesizer. The amplification reaction was carried out in a total volume of 50 µl in the presence of 0.8 mM MgCl$_2$, 10 mM Tris-HCl (pH 8.3), 50 mM KCl, 0.01% gelatine, 0.2 mM dATP, 0.2 mM dGTP, 0.2 mM dTTP, 0.2 mM dCTP, each primer (0.25 µM), 400–600 ng of genomic DNA as template and 1.5 U of Taq polymerase (BRL, Bethesda Research Laboratories). After an initial melting period at 94° C. for 1 min30s, 30 to 35 cycles of 1 min at 94° C., 1 min30s at 52° C., 1 min30s at 72° C., and a final extension period of 7 min at 72° C. were done. Following this, 10 µl of each sample was analysed on a 1.2% agarose gel. DNA of an individual homozygous for the XbaI-11.5 kb allele was used as a negative control, since this allele lacks the CYP2D6 gene (Gaedigk et al., Naunyn-Schmiedeberg's *Archives of Pharmacology* 341 (Supplement), *Abstract* 435 [1990]).

Example 3

Allele Specific Amplification

In the second PCR reaction (allele-specific amplification) the primer pair 4/5 amplified a 588bp fragment from 29-wt and 29-B alleles of fragment A, both lacking the frameshift mutation in exon 5. The primer pair 4/6 amplified a fragment of the same length from 29-A alleles only. The 29-B allele was unambiguously identified by amplification of a 564bp fragment from fragment B with the primer pair 1/8, whereas amplification from the 29-wt and 29-A alleles occurred only with the primer pair 1/7 (FIG. 8 and 9).

1 µl of the reaction of Example 2 was used as template in two parallel allele specific reactions, one with a "wild-type specific primer" and the other with a "mutation specific primer". The second primer in both cases was the "common primer" 1 and 4 already used in the first PCR reaction in Example 2; Fragment A therefore was amplified once with primers 4 and 5 (GCTAACTGAGCACA SEQ ID NO:7, from 2624–2637) and once with primers 4 and 6 (GCTAACTGAGCACG, G SEQ ID NO:8 at position 2637), fragment B once with primers 1 and 7 (CGAAAGGGGCGTCC, SEQ ID NO:3 from 1934–1947) and once with primers 1 and 8 (CGAAAGGGGCGTCT, SEQ ID NO:4 T at position 1947). The amplification of fragment B is especially shown in FIG. 8B. The reaction conditions were chosen to allow amplification only in case of a perfect match between primer and template DNA. They were as follows: total volume 50 µl; 0.8 mM MgCl$_2$, 10 mM Tris-HCl pH 8.3, 50 mM KCL, 0.01% gelatine, 0.2 mM each dNTP, 0.25 µM each primer, 1 U of Taq polymerase. 15 cycles were allowed to proceed with 1 min at 94° C., 1 min at 50° C. and 1 min at 72° C. 10 µl of each sample were analysed on a 1.2% agarose gel. The DNA from 3 PM individuals with previously sequenced CYP2D6-alleles served as control for this second PCR reaction.

Example 4

Detection and analysis

The combined results of all four reactions described in Example 3 allowed the determination of both alleles in individuals with the XbaI 29/29 kb genotype and of the 29 kb allele in individuals with the XbaI 11.5/29 kb or XbaI 44/29 kb genotpye. The 3 possible results for each mutation are exemplified for the splice-site mutation of the 29-B allele in FIG. 9. Subject #18 has no 29-B allele, #37 has one 29-B allele and #13 one or two 29-B alleles. Results from the 29-A allele-specific amplification can be interpreted in the same way. Thus, #18 and #13 had no 29-A allele, #37 had one. Combined, these data reveal the following genotypes: 29-wt/29-wt for #18, 29-A/29-B for #37 and 29-B/29-B for #13, consistent with their phenotypes of EM, PM and PM respectively.

No false positive or false negative results were observed using the DNA of three PM individuals with known sequences of both CYP2D6 alleles and of seven individuals of known phenotype with an informative 11.5 kb/29 kb XbaI-genotype, where the 29 kb allele must correspond to the phenotype. From 9 PMs with the XbaI 29/29 pattern, 6 were homozygous for the 29-B allele, the remaining three were heterozygous 29-A/29-B. From 6 PMs with the XbaI 29/11.5 pattern, five had a 29-B allele and one a 29-A allele. Of 22 EMs (XbaI 29/29 kb) 10 were homozygous for the 29-wt allele, 9 were heterozygous for the 29-wt/29-B alleles and three heterozygous for the 29-wt/29-A.

Example 5

Detection of Slow acetylation polymorphism by allele-specific amplification

The knowledge on the mutations of the NAT2 alleles designated as M1 and M2 (FIG. 10b) as well as that on a third mutant allele, M3, recently reported by Ohsako et al. infra, was used to develop a set of mutation-specific primers for allele-specific amplification of small amounts of DNA by the polymerase chain reaction (PCR). The study population was composed of 18 in vivo phenotyped individuals (caffeine test, 14) and of 26 in vitro phenotyped liver samples (sulfamethazine acetylation, 7). 24 were classified as slow and 20 as rapid acetylators. Our test predicted correctly 19 of the 20 rapid and 22 of the 24 slow acetylator phenotypes. Of the identified 65 slow alleles, M1 accounted for 30 alleles (46%), M2 for 32 alleles (49%) and M3 for only 3 alleles (5%).

The following detailed description shows the use and sequences of the specific primers employed in the detection of the wt and of the three mutant alleles (M1, M2 and M3). The mutation responsible for the M3 allele was described by Ohsako et al. in *J: of Biol. Chem.* 265, 4630–4634 (1990) in having a mutation at position 857 which is a G (wt) to A (M3) exchange in the NAT2 gene.

Specific primers for the wt and the mutant alleles M1, M2 and M3 were used in separate PCR reactions. Primer "M1 wt" (CTGATTTGGTCCAG) SEQ ID NO:10 is complementary to the NAT2 gene at position 481 to 494, primer "M1 mut" (CTGATTTGGTCCAA) SEQ ID NO:11 recognizes the mutation $C_{481}$ to T of M1; primers "M2 wt" (574 to 590, TTTACGCTTGAACCTCG) SEQ ID NO:13 and "M2 mut" (574 to 590, TTTACGCTTGAACCTCA) SEQ ID NO:14 test for the presence of the mutation $G_{590}$ to A of M2, primers "M3 wt" (857 to 870, AATAGTAAGGGATC) SEQ ID NO:15 and "M3 mut" (857 to 870, AATAGTAAGGGATT) SEQ ID NO:16 test for the mutation $G_{857}$ to A of M3. The common primer used for the reactions with primers M1 wt, M1 mut, M3 wt and M3 mut is "primer 1" (-74 to -58, AATTAGTCACACGAGGA) SEQ ID NO:9, for the reactions with primers "M2 wt" and "M2 mut" it is "primer 2" (1119 to 1138, TCTAGCATGAATCACTCTGC) SEQ ID NO:12.

All PCR reactions were carried out in a total volume of 50µl in the presence of 10 mM Tris-HCl, pH 8.3, 50 mM KCl, 0.01% (w/v) gelatin, 0.2 mM of each dNTP, 0.5 µM of each primer, 1.25 U Taq Polymerase (Bethesda Research Laboratories), 300–600ng genomic DNA, and either 1.5 mM MgCl$_2$ (primers "M1 wt" and "M1 mut"), or 1.25 mM MgCl$_2$(M$_2$ wt" and "M2 mut") or 1.75mM MgCl$_2$ (M3 wt" and "M3 mut"). 30 cycles (60s at 94° C., 90s at 48° C. (M1)/55° C.(M2)/35° C. (M3) 3 min at 72° C.) were carried out followed by a final extension period of 7 min at 72° C. 10 µl of each sample was analysed on a 1.5% agarose gel.

First subjects were classified as slow or rapid acetylator phenotypes by conventional methods (caffeine test). Afterwards, allele-specific amplification by PCR was performed on DNA of these individuals to detect the three possible mutations associated with slow acetylation using the primers and methods described above.

The result of the corresponding PCR reactions is shown in lanes 1–6 of FIG. 11. The mutation specific primer (mut) for M1 (lane 2) and M2 (lane 4) both yield the correct amplification products (568bp and 565bp), whereas no band is visible after amplification with the M3 specific primer (lane 6). The DNA of the subject exemplified in lanes 1–6 therefore has one M1 and one M2 allele. The primer complementary to the wild-type NAT2 gene at the site of mutation M1 predictably leads to amplification from allele M2 (lane 1), the corresponding "wild-type primer" of M2 binds to allele M1 (lane 3), and the "wild-type primer" of M3 amplifies both alleles of this subject (lane 5, 944bp fragment).

While the invention has been described in conjunction with preferred embodiments, the foregoing description and examples hereinafter are not intended to limit the scope of the invention.

I claim:

1. A primer comprising a nucleic acid sequence of 10 to 25 bases, said primer being capable of amplifying by the polymerase chain reaction a nucleic acid sequence of an allele of the CYP2D6 gene coding for the cytochrome P450 isozyme P450IID6, said sequence of said allele having a mutated or wild type sequence, said primer containing at the 3' end at least one base complementary to base number 1062, 1072, 1085, 1749, 1934, 2637 or 4268 of the wild type or mutated CYP2D6 gene sequence and having bases in the 5' direction which are sufficiently complementary to said gene to hybridize therewith.

2. The primer of claim 1, which comprises the sequence:

5'CGA AAG GGG CGT CC3'(SEQ ID NO:3).

3. The primer of claim 1, which comprises the sequence:

5'CGA AAG GGG CGT CT3'. (SEQ ID NO:4).

4. The primer of claim 1, which comprises the sequence:

5'GCT AAC TGA GCA CA 3'. (SEQ ID NO:7).

5. The primer of claim 1, which comprises the sequence:

5'GCT AAC TGA GCA CG3'(SEQ ID NO:8).

* * * * *